United States Patent [19]

LaVallée et al.

[11] Patent Number: 5,693,619
[45] Date of Patent: Dec. 2, 1997

[54] METHOD OF USING RENIN INHIBITING N-(2-AMINO-2-OXOETHYL) BUTANEDIAMIDE DERIVATIVES

[75] Inventors: Pierre LaVallée, Rosemère; Bruno Simoneau, Laval, both of Canada

[73] Assignee: Boehringer Ingelheim (Canada), Ltd., St., Laval, Canada

[21] Appl. No.: 595,327

[22] Filed: Feb. 1, 1996

Related U.S. Application Data

[60] Division of Ser. No. 122,280, Sep. 17, 1993, Pat. No. 5,516,760, which is a continuation-in-part of Ser. No. 951,478, Sep. 25, 1992, abandoned.

[51] Int. Cl.⁶ ................................. A61K 38/00
[52] U.S. Cl. .................... 514/19; 514/231.2; 514/231.5; 514/231.8; 514/315; 514/336; 514/342; 514/381; 514/382; 514/396; 514/408; 514/438; 514/439; 514/461
[58] Field of Search ...................... 514/19, 231.2, 514/231.5, 231.8, 315, 336, 342, 381, 382, 392, 408, 438, 439, 461

*Primary Examiner*—Gary Geist
*Assistant Examiner*—Deborah D. Carr
*Attorney, Agent, or Firm*—R. P. Raymond; M-E. M. Devlin; A. R. Stempel

[57] ABSTRACT

Disclosed herein is a method of using compounds of the formula:

$$A-N(R^1)C(O)CH_2CHR^2C(O)-B$$

wherein A is $R^3R^4NC(O)CH_2$ when, for example, $R^3$ is hydrogen or alkyl and $R^4$ is hydrogen, alkyl or a substituted alkyl such as 2-(2-pyridinyl)ethyl, or $R^3$ and $R^4$ together with the nitrogen atom to which they are attached form a pyrrolidino, piperidino, morpholino or thiomorpholino; $R^1$ is, for example, benzyl, alkyl or a substituted alkyl such as cyclohexylmethyl; $R^2$ is, for example, alkyl, cycloalkylmethyl, 1H-imidazol-4-ylmethyl, 4-thiazolylmethyl or (2-amino-4-thiazolyl)methyl; and B is a renin substrate transition state analog, for example, [1(S)-(cyclohexylmethyl)-2(R),3(S)-dihydroxy-5-methylhexyl] amino for the treatment of congestive heart failure.

5 Claims, No Drawings

METHOD OF USING RENIN INHIBITING N-(2-AMINO-2-OXOETHYL) BUTANEDIAMIDE DERIVATIVES

This is a division of application Ser. No. 08/122,280, filed Sep. 17, 1993, now U.S. Pat. No. 5,516,160, which is a continuation-in-part of application Ser. No. 07/951,478, filed Sep. 25, 1992, now abandoned.

FIELD OF INVENTION

This invention relates to compounds exhibiting renin inhibiting properties, to processes for producing the compounds, to pharmaceutical compositions thereof, to processes and intermediates for preparing the compounds and to methods of treating renin-dependent hypertension and congestive heart failure.

BACKGROUND OF THE INVENTION

The physiological role of the renin-angiotensin system is to regulate blood pressure and to maintain sodium and volume homeostasis. The key events in this system are the conversion of the polypeptide angiotensinogen to the decapeptide angiotensin I (AI) and the subsequent cleavage of the latter to give the octapeptide angiotensin II (AII). The latter peptide is a potent vasoconstrictor and a potentiator of aldosterone release. Due to potent pressor effects, AII plays a significant role in hypertension and as such has been the target for the development of antihypertensive agents.

One approach to finding such agents is to search for potent inhibitors of the angiotensin converting enzyme. Inter alia, the latter enzyme catalyzes the conversion of AI to AII. This approach has met with success and a number of such agents are used therapeutically to treat hypertension. Another approach is to find specific inhibitors of renin, an aspartyl protease which cleaves angiotensinogen to AI. Since angiotensinogen is the only known natural substrate for renin, this approach has the desirable feature of being aimed at a potential antihypertensive agent with a single mode of action.

In the pursuit of this goal, a great deal of attention has been given to designing renin inhibitors which mimic the natural substrate angiotensinogen. Much of this effort has been focused on the design of analogous substrates incorporating therein a non-cleavable mimic (i.e. a transition state analog) of the renin cleavage site (i.e. Leu-Val) of human angiotensinogen. As a result, a number of potent renin inhibitors have been identified in the laboratory, and the ability of renin inhibitors to lower blood pressure and to reduce plasma renin activity has now been demonstrated in the clinic. For a recent review on renin inhibitors, see W. J. Greenlee, Medical Research Reviews, 10, 173 (1990). Nevertheless, progress toward obtaining the ideal renin inhibitor continues to be plagued with problems of low oral absorption, limited bioavailability and rapid elimination, mainly due to the peptidic nature of the inhibitors presently under investigation. Hence, there is a need for a readily administered, effective renin inhibitor.

The renin inhibitors of the present application belong to the class of transition state analog inhibitors of renin. They are characterized by having a N-(amidomethyl)succinamoyl moiety incorporated into their structure. This feature, in combination with their non-peptidic character and their relatively lower molecular weight, apparently contribute beneficially to the stability, absorption and bioavailability of the inhibitors. Another feature of the present inhibitors is their relative specificity for renin as compared to other aspartyl proteases.

The following references exemplify past efforts that have been made in the search for renin inhibitors with improved characteristics:

W. J. Greenlee et al., European patent application 278 158, published Aug. 17, 1988;

A. A. Patchett et al., U.S. Pat. No. 4,839,357, issued Jun. 13, 1989;

D. J. Kempf et al., European patent application 402 646, published Dec. 19, 1990;

P. D. Williams et al., U.S. Pat. No. 5,001,113, issued Mar. 19, 1991;

H. Heitsch et al., Canadian patent application 2,025,093, published Mar. 13, 1991;

W. J. Greenlee et al., U.S. Pat. No. 5,006,511, issued Apr. 9, 1991;

P. D. Williams, Cannadian patent application 2,034,524, published Jul. 20 ,1991;

H. N. Weller and D. E. Ryono, U.S. Pat. No. 5,055,466, issued Oct. 8, 1991; and

S. H. Rosenberg et al., U.S. Pat. No. 5,063,208, issued Nov. 5, 1991.

SUMMARY OF THE INVENTION

The compounds of the present application are represented by formula 1

$$A\text{-}N(R^1)C(O)CH_2CH(R^2)C(O)\text{-}B \qquad (1)$$

wherein A is $R^3R^4NC(O)CH_2$ wherein (a) $R^3$ is hydrogen or lower alkyl and $R^4$ is hydrogen, lower alkyl or lower alkyl monosubstituted with lower cycloalkyl, phenyl, or a heterocylic ring (hereinafter designated as "Het") which is an unsubstituted, monosubstituted or disubstituted, five- or six-membered ring containing one or two heteroatoms selected from the group consisting of N, O and S, and wherein each substituent is selected independently from the group consisting of lower alkyl, lower alkoxy, halo, amino or lower alkylamino; or (b) $R^3$ is lower alkyl and $R^4$ is $R^5R^6N$-Alk wherein $R^5$ and $R^6$ each is hydrogen or lower alkyl and Alk is a divalent alkyl radical derived by the removal of two hydrogen atoms of a straight or branched chain hydrocarbon containing from one to six carbon atoms; or (c) $R^3$ is lower alkyl and $R^4$ is $R^{5A}R^{6A}NCH_2CH_2$ wherein $R^{5A}$ is lower alkyl and $R^{6A}$ is piperidinocarbonyl, morpholinocarbonyl, thiomorpholinocarbonyl, piperazinocarbonyl or 4-(lower alkyl)-1-piperazinylcarbonyl; or (d) $R^3$ is lower alkyl and $R^4$ is $QC(O)(CH_2)_m$ wherein Q is piperidino, morpholino, thiomorpholino, piperazino or 4-(lower alkyl)-1-piperazinyl and m is the integer 1 or 2; or (e) $R^3$ is lower alkyl and $R^4$ is lower alkoxy; or (f) $R^3$ and $R^4$ together with the nitrogen atom to which they are attached form a pyrrolidino, piperidino, 4-hydroxy-1-piperidinyl, 4-[(lower alkoxy)-(lower alkoxy)]-1-piperidinyl, morpholino, thiomorpholino, piperazino or 4-(lower alkyl)-1-piperazinyl;

$R^1$ is (1–8C)alkyl or lower alkyl monosubstituted with lower cycloalkyl, 1-(lower alkyl)-(lower cycloalkyl), bicyclo[2.2.1]hept-2-yl, phenyl, 2-(lower alkyl)phenyl, 2-(lower alkoxy)phenyl, 2-halophenyl, 4-(lower alkyl)phenyl, 4-(lower alkoxy)-phenyl, 4-halophenyl, 3,5-di(lower alkyl)phenyl, (3,4-methylenedioxy)phenyl, 1-naphthyl, 2-naphthyl or Het wherein Het is as defined hereinabove;

$R^2$ is lower alkyl, (lower cycloalkyl)methyl, benzyl or Het-$CH_2$ wherein Het is as defined hereinabove; and B is a transition state analog of the formula $NHCH(R^7)CH(OH)$-Z wherein $R^7$ is lower alkyl, (lower cycloalkyl)

methyl, benzyl, [4-(lower alkyl)phenyl]methyl, [4-(lower alkoxy)phenyl]methyl, or (4-halophenyl)methyl, and Z is lower alkyl, lower cycloalkyl, (lower cycloalkyl)methyl, $C(O)OR^8$ wherein $R^8$ is lower alkyl, the radical of formula 2

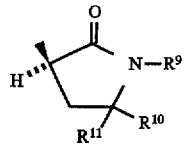

wherein $R^9$ is lower alkyl and $R^{10}$ and $R^{11}$ each is hydrogen or lower alkyl, [(1-methyl-1H-tetrazol-5-yl)thio]methyl or $CH(OH)R^{12}$ wherein $R^{12}$ is lower alkyl or lower cycloalkyl, with the provisos (1) that the asymmetric carbon atom bearing $R^7$ has the (S) configuration, (2) that when Z is lower alkyl, lower cycloalkyl, (lower cycloalkyl)methyl or the radical of formula 2 as defined hereinabove then the asymmetric carbon atom bearing the hydroxyl in the $NHCH(R^7)$ CH(OH) radical has the (S) configuration, (3) that when Z is $C(O)OR^8$ wherein $R^8$ is lower alkyl, or when Z is [(1-methyl-1H-tetrazol-5-yl)thio]-methyl, then the asymmetric carbon atom bearing the hydroxyl in the $NHCH(R^7)$ CHOH radical has the (R) configuration, and (4) that when Z is $CH(OH)R^{12}$ wherein $R^{12}$ is lower alkyl or lower cycloalkyl then the asymmetric carbon atoms bearing the hydroxyls in the $NHCH(R^7)CH(OH)$ and Z radicals have respectively the (R) and (S) configuration; with the additional proviso that the carbon atom bearing $R^2$ has the (R) configuration, except when $R^2$ is $CH_2$-Het wherein Het has a nitrogen atom at the point of attachment, and/or Het contains a sulfur atom next to the atom (C or N) at the point of attachment, of the Het to the methylene ($CH_2$), then in the instance of this exception the carbon atom bearing $R^2$ has the (S) configuration; or a therapeutically acceptable acid addition salt thereof.

A preferred group of the compounds of the present application is represented by formula 1 wherein A is $R^3R^4NC(O)CH_2$ wherein (a) $R^3$ is lower alkyl and $R^4$ is lower alkyl or lower alkyl monosubstituted with phenyl or Het wherein Het is as defined hereinabove;

(b) $R^3$ is lower alkyl and $R^4$ is $R^5R^6N$-Alk wherein $R^5$ and $R^6$ each is lower alkyl and Alk is as defined hereinabove;

(c) $R^3$ is lower alkyl and $R^4$ is $R^{5A}R^{6A}NCH_2CH_2$ wherein $R^{5A}$ is lower alkyl and $R^{6A}$ is piperidinocarbonyl, morpholinocarbonyl or 4-methyl-1-piperazinylcarbon-yl; or (d) $R^3$ is lower alkyl and $R^4$ is 2-morpholino-2-oxoethyl, 3-morpholino-3-oxopropyl or 3-(4-methyl-1-piperazinyl)-3-oxopropyl; or (e) $R^3$ is lower alkyl and $R^4$ is lower alkoxy; or (f) $R^3$ and $R^4$ together with the nitrogen atom to which they are attached form a pyrrolidino, piperidino, 4-hydroxy-1-piperidinyl, 4-(methoxymethoxy)-1-piperidinyl, morpholino, thiomorpholino or 4-methyl-1-piperazinyl;

$R^1$ is (1-8C)alkyl or lower alkyl monosubstituted with lower cycloalkyl, 1-(lower alkyl)-(lower cycloalkyl), bicyclo [2.2.1]hept-2-yl, phenyl, 2-methylphenyl, 2-fluorophenyl, 4-methylphenyl, 4-methoxyphenyl, 4-chlorophenyl, 4-fluorophenyl, 3,5-dimethylphenyl, (3,4-methylenedioxy)phenyl, 1-naphthyl, 2-naphthyl or Het wherein Het is as defined hereinabove;

$R^2$ is lower alkyl, (lower cycloalkyl)methyl, benzyl, 1H-imidazol-2-ylmethyl, 1H-imidazol-4-ylmethyl, (1-methyl-1H-imidazoyl-4-yl)methyl, 2-thienylmethyl, 2-oxazolylmethyl, 4-oxazolylmethyl, 2-thiazolylmethyl, 4-thiazolylmethyl, (2-methyl-4-thiazolyl)methyl, (2-amino-4-thiazolyl)methyl, [2-(methylamino)-4-thiazolyl]methyl, 2-pyridinylmethyl or 3-pyridinylmethyl; and B is as defined in the last instance; or a therapeutically acceptable acid addition salt thereof.

A more preferred group of compounds is represented by formula 1 wherein A is $R^3R^4NC(O)CH_2$ wherein $R^3$ is methyl, ethyl or propyl and $R^4$ is methyl, ethyl, propyl 1,1-dimethylethyl, 2-(dimethylamino)ethyl, 2-(diethylamino)ethyl, or Het-$(CH_2)_n$ wherein Het is 2-pyrrolyl, 2-furanyl, 2-thienyl, 1H-imidazol-2-yl, 1H-imidazol-4-yl, 2-isoxazolyl, 2-thiazolyl, 4-thiazolyl, 2-amino-4-thiazolyl, morpholino, 4-methyl-1-piperazinyl, 2-pyridinyl, 3-pyridinyl, 4-pyridinyl or 2-pyrimidinyl and n is the integer 1, 2 or 3; or $R^3$ is methyl and $R^4$ is 2-[methyl (morpholinocarbonyl)amino]ethyl or 2-{methyl[(4-methyl-1-piperazinyl) carbonyl]amino}-ethyl; or $R^3$ is methyl and $R^4$ is 3-morpholino-3-oxopropyl or 3-(4-methyl-1-piperazinyl)-3-oxopropyl; or $R^3$ is methyl and $R^4$ is methoxy; or $R^3$ and $R^4$ together with the nitrogen to which they are attached form a pyrrolidino, piperidino, 4-hydroxy-1-piperidinyl, 4-(methoxymethoxy)-1-piperidinyl, morpholino or 4-methyl-1-piperazinyl; $R^1$ is 2-methylpropyl, 2-ethylbutyl, 1-propylbutyl, 2-propylpentyl, cyclopentylmethyl, 2-cyclopentylethyl, cyclohexylmethyl, (S)-1-cyclohexylethyl, 2-cyclohexylethyl, cycloheptylmethyl, (1-methylcyclohexyl)methyl, (1-methylcycloheptyl)methyl, (bicyclo[2.2.1]hept-2-yl) methyl, benzyl, (S)-1-phenylethyl, 2-phenylethyl, (R or S)-2-phenylpropyl, 2-methyl-2-phenylpropyl, 3-phenylpropyl, (2-fluorophenyl)methyl, (2-methylphenyl) methyl, (4-methoxyphenyl)methyl, (4-chlorophenyl)methyl, (4-fluorophenyl)methyl, (3,5-dimethylphenyl)methyl, 1-naphthylmethyl, (S)-[1-(1-naphthyl)ethyl], 2-naphthylmethyl, 2-pyrrolylmethyl, 1H-imidazol-2-ylmethyl, 1H-imidazol 4-ylmethyl, 2-pyridinylmethyl, 3-pyridinylmethyl, 2-furanylmethyl, 3-furanylmethyl 2-thienylmethyl, (3-methyl-2-thienyl)methyl, 2-oxazolymethyl, 4-oxazolylmethyl, 2-thiazolylmethyl or (2-amino-4-thiazolyl)methyl; $R^2$ is propyl, 2-methylpropyl, cyclopropylmethyl, cyclopentylmethyl, cyclohexyl-methyl, benzyl, 1H-imidazol-2-ylmethyl, 1H-imidazol-4-ylmethyl, (1-methyl-1H-imidazol-4-yl)methyl, 2-thienylmethyl, 2-oxazolylmethyl, 4-oxazolylmethyl, 2-thiazolylmethyl, 4-thiazolylmethyl, (2-methyl-4-thiazolyl)methyl, (2-amino-4-thiazoly)methyl, [2-(methylamino)-4-thiazolyl]-methyl, 2-pyridinylmethyl or 3-pyridinylmethyl; and B is [1(S)-(2-methylpropyl)-2(S)-hydroxy-5-methylhexyl]amino, [1l(S)-(cyclohexylmethyl)-2(S)-hydroxy-5-methylhexyl]amino, [1(S)-[(4-methoxyphenyl)methyl]-2(S)-hydroxy-5-methylhexyl]amino, [1(S)-(cyclohexylmethyl)-2-(S)-hydroxy-4-methylpentyl]amino, [1(S)-(cyclohexylmethyl)-2(S)-hydroxy-(3-cyclopropylpropyl)]amino, [1(S)-(2-methylpropyl)-2(R),3(S)-dihydroxy-5-methylhexyl]amino, [1(S)-(cyclohexylmethyl)-2(R),3(S)-dihydroxy-5-methylhexyl]amino, {1(S)-[(4-methoxyphenyl)methyl]-2 (R),3(S)-dihydroxy-5-methylhexyl}amino, [1(S)-(2-methylpropyl)-2(R),3(S)-dihydroxy-(3-cyclopropylpropyl)] amino, [1(S)-(cyclohexylmethyl)-2(R),3(S)-dihydroxy-(3-cyclopropylpropyl)]amino, [1(S)-(phenylmethyl)-2(R),3(S) -dihydroxy-(3-cyclopropylpropyl)]amino, {1(S)-[(4-methoxyphenyl)methyl]-2(R),3(S)-dihydroxy-(3-cyclopropylpropyl)]amino, [1(S)-(cyclohexylmethyl)-2(R)-hydroxy-3-(1-methylethoxy)-3-oxopropyl]-amino, [1(S)-(cyclohexylmethyl)-2(S)-hydroxy-2-(1,5,5-trimethyl-2-oxopyrrolidin-3(S)-yl) ethyl]amino or {1(S)-(cyclohexylmethyl)-2(R)-hydroxy-3-[(1-methyl-1H- tetrazol-5-yl)thio]propyl}amino; or a therapeutically acceptable acid addition salt thereof.

A most preferred group of the compound is represented by formula 1 wherein A is $R^3R^4NC(OC)CH_2$ wherein $R^3$ is methyl and $R^4$ is methyl, 2-(dimethylamino)ethyl, 2-(diethylamino)ethyl, 2-(2-pyrrolyl)ethyl, 2-(2-furanyl) ethyl, 2-(1H-imidazol-2-yl)ethyl, 2-(1H-imidazol-4-yl) ethyl, 2-(2-thiazolyl)ethyl, 2-morpholinoethyl, 2-(2-pyidinyl)ethyl, 2-(3-pyridinyl)ethyl, 2-(4-pyridinyl)ethyl or 2-(2-pyrimidinyl)ethyl; or $R^3$ is methyl and $R^4$ is 2-[methyl (morpholinocarbonyl)amino]ethyl; or $R^3$ is methyl and $R^4$ is methoxy; or $R^3$ and $R^4$ together with the nitrogen atom to which they are attached form a pyrrolidino, piperidino, 4-hydroxy-1-piperidinyl, 4-(methoxy-methoxy)-1-piperidinyl, morpholino or 4-methyl-1-piperazinyl; $R^1$ is 2-ethylbutyl, 1-propylbutyl, 2-propylpentyl, cyclopentylmethyl, 2-cyclopentylethyl, cyclohexylmethyl, (S)-1-cyclohexylethyl, cycloheptylmethyl, (bicyclo[2.2.1] hept-2-yl)methyl, benzyl, (S)-1-phenylethyl, 2-phenylethyl, (S)-2-phenylpropyl, (R)-2-phenylpropyl, (2-fluorophenyl) methyl, (2-methylphenyl)methyl, (3,5-dimethylphenyl) methyl, 1-naphthylmethyl, 2-furanylmethyl, 3-furanylmethyl, 2-thienylmethyl, (3-methyl-2-thienyl) methyl or 2-thiazolylmethyl; $R^2$ is propyl, cyclopropylmethyl, 1H-imidazol-4-ylmethyl, (1-methyl-1H-imidazol-4-yl)methyl, 2-thienylmethyl, 2-oxazolylmethyl, 4-oxazolylmethyl, 2-thiazolylmethyl, 4-thiazolylmethyl, (2-methyl-4-thiazolyl)methyl or (2-amino-4-thiazolyl)methyl; and B is [1(S)-(cyclohexylmethyl)-2(S)-hydroxy-5-methylhexyl]amino, [1(S)-(cyclohexylmethyl)-2(S)-hydroxy-(3-cyclopropylpropyl)]amino, [1(S)-(cyclohexylmethyl)-2(R), 3(S)-dihydroxy-(3-cyclopropylpropyl)]amino, [1(S)-(cyclohexylmethyl)-2(R),3(S)-dihydroxy-5-methylhexyl]-amino, [1(S)-(cycohexylmethyl)-2(R)-hydroxy-3-(1-methylethoxy)-3-oxopropyl]amino or [1(S)-(cyclohexylmethyl)-2-(S)-hydroxy-2-(1,5,5-trimethyl-2-oxopyrrolidin-3(S)-yl)ethyl]amino; or a therapeutically acceptable acid addition salt thereof.

Included within the scope of this invention is a pharmaceutical composition for treating renin-dependent hypertension comprising a compound of formula 1, or a therapeutically acceptable acid addition salt thereof, and a pharmaceutically acceptable carrier.

Also included in this invention is a method of treating renin-dependent hypertension or congestive heart failure in a mammal comprising administering thereto a blood pressure-lowering effective amount of the compound of formula 1, or a therapeutically acceptable acid addition salt thereof.

Processes for preparing the compounds of formula 1 are described hereinafter.

DETAILS OF THE INVENTION

GENERAL

With reference to the instances where (R) or (S) is used to designate the configuration of a radical, e.g. $R^1$ of the compound of formula 1, the designation is done in the context of the compound and not in the context of the radical alone.

The term "Alk" as used herein means a divalent alkyl radical derived by the removal of two hydrogen atoms from a straight or branched chain aliphatic hydrocarbon containing from one to six carbon atoms and includes, for example, —$CH_2CH_2$—, —$CH_2CH_2CH_2$—, —$CH(CH_3)CH_2CH_2$— and —$(CH_2)_6$—.

The term "lower alkyl" as used herein, either alone or in combination with another radical, means straight chain alkyl radicals containing one to four carbon atoms and branched chain alkyl radicals containing three to four carbon atoms and includes methyl, ethyl, propyl, butyl, 1-methylethyl, 1-methylpropyl, 2-methylpropyl and 1,1-dimethylethyl.

The term "(1–8C)alkyl" as used herein means straight and branched chain alkyl radicals containing from one to eight carbon atoms and includes ethyl, butyl, 1-methylpropyl, 2-methylpropyl, 1-ethylpropyl, 2-ethylbutyl, 2-propylpentyl and the like.

The term "lower cycloalkyl" as used herein, either alone or in combination with a radical, means saturated cyclic hydrocarbon radicals containing from three to ten carbon atoms and includes cyclopropyl, cyclobutyl, cyclopentyl, cyclohexyl and cycloheptyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "halo" as used herein means a halo radical selected from bromo, chloro, fluoro or iodo.

The term "Het" as used herein means a monovalent radical derived by removal of a hydrogen from a five- or six-membered saturated or unsaturated heterocycle containing from one to two heteroatoms selected from nitrogen, oxygen and sulfur. Optionally, the heterocycle may bear one or two substituents; for example, lower alkyl, lower alkoxy, halo, amino or lower alkylamino. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, 3-methylthiophene, oxazole, isoxazole, thiazole, 2-methylthiazole, 2-aminothiazole, 2-(methylamino)-thiazole, piperidine, 1-methylpiperazine, 1,4-dioxane, morpholine, pyridine, pyrimidine and 2,4-dimethylpyrimidine.

The term "coupling agent" as used herein means an agent capable of effecting the dehydrative coupling of a carboxy group of one compound with a free amino group of another compound to form an amide bond between the reactants. The agents promote or facilitate the dehydrative coupling by activating the carboxy group. Descriptions of such coupling agents and activated groups are included in general textbooks of peptide chemistry; for instance, E. Schröder and K. L. Lübke, "The Peptides", Vol. 1, Academic Press, New York, N.Y., 1965, pp 2–128, and "The Peptides: Analysis, Synthesis, Biology", E. Grass et al., Eds., Academic Press, New York, N.Y., USA, 1979–1987, Volumes 1 to 9. Examples of suitable coupling agents are 1,1-carbonyldiimidazole or N,N-dicyclohexylcarbodiimide. Other examples are 1-hydroxybenzotriazole in the presence of N,N-dicyclohexylcarbodiimide or N-ethyl-N-[(3-dimethylamino)propyl]carbodiimide. A very practical and useful coupling agent is the commercially available (benzotriazol-1-yloxy)tris-(dimethylamino)-phosphonium hexafluorophosphate, either by itself or in the presence of 1-hydroxybenzotriazole. Still another very practical and useful coupling agent is the commercially available 2-(1H-benzotriazol-1-yl)-N,N,N,N-tetramethyluronium tetrafluoroborate.

The term "pharmaceutically acceptable carrier" as used herein means a non-toxic, generally inert vehicle for the active ingredient, which does not adversely affect the ingredient.

The term "effective amount" as used herein means a predetermined amount of the compound of formula 1 sufficient to lower blood pressure on being administered to a mammal.

Process

In general, the compounds of formula 1 are prepared by known methods using reaction conditions which are known to be suitable for the reactants. Description of the methods are found in standard textbooks such as "Annual Reports In Organic Synthesis—1990", K. Turnbull et al., Eds, Academic Press, Inc., San Diego, Calif., USA, 1990 (and the preceding annual reports), "Vogel's Textbook Of Practical Organic Chemistry", B. S. Furniss et al., Eds, Longman Group Limited, Essex, UK, 1986, and "The Peptides: Analysis, Synthesis, Biology", E. Grass et al., Eds, Academic Press New York, N.Y., USA, 1979–1987, Volumes 1 to 9.

Since the compounds of formula 1 contain two amide bonds, a convenient and practical approach to preparing the compounds is based on the step-wise coupling of the appropriate fragments, i.e. precursors for the amide bond formations.

A common feature of the coupling of the fragments, which involves the reaction of a free amino function of one fragment with a free carboxy function of another fragment, is the protection of competing reactive sites, if present, on the fragments. Such protection is provided by the use of known protective groups which will prevent a chemical reaction from occurring at the competing site during the coupling step and which can ultimately be removed after completion of the coupling to afford the desired product. The protective groups and the deprotecting agents for removing the group are selected according to conventional practice. See J. W. Greene and P. G. M. Wuts, "Protective Groups In Organic Synthesis", 2nd ed., John Wiley & Sons, Inc., New York, N.Y., USA, 1991 for a full description of protective groups and deprotective agents.

More explicitly, a process for preparing the compounds of formula 1, involving the stepwise coupling of appropriate fragments in which competing reactive sites, if present, are protected by suitable protective groups, comprises:

(a) coupling a monoprotected dicarboxylic acid of formula 2

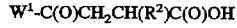

$W^1\text{-C(O)CH}_2\text{CH(R}^2\text{)C(O)OH}$     2 wherein $W^1$ is a carboxy protecting group and $R^2$ is as defined hereinbefore with an amine of formula H-B wherein B is as defined herein to obtain the corresponding protected amido acid of formula 3

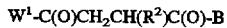

$W^1\text{-C(O)CH}_2\text{CH(R}^2\text{)C(O)-B}$     3 wherein $W^1$, $R^2$ and B are as defined hereinbefore; po0 (b) reacting the latter compound with a deprotecting agent to obtain the corresponding amido acid of formula 4

$\text{HO-C(O)CH}_2\text{CH(R}^2\text{)C(O)-B}$     4 wherein $R^2$ and B are as defined hereinbefore; and (c) coupling the latter amido acid with an amine of formula $\text{ANH(R}^1\text{)}$ wherein A and $R^1$ are as defined hereinbefore; and, if required, eliminating any protective groups on the instant product used to protect competing reactive sites during the process, to obtain the corresponding compound of formula 1.

Alternatively, the compounds of formula 1 can be prepared by an analogous process comprising:

(d) coupling an amine of formula $\text{ANH(R}^1\text{)}$ in which A and $R^1$ are as defined hereinbefore with a monoprotected dicarboxylic acid of formula 5

$\text{HO-C(O)CH}_2\text{CH(R}^2\text{)C(O)-W}^2$     5 wherein $R^2$ is as defined herein and $W^2$ is a carboxy protective group to obtain the corresponding protected amido acid of formula 6

$\text{A-N(R}^1\text{)C(O)CH}_2\text{CH(R}^2\text{)C(O)-W}^2$     6 wherein A, $R^1$, $R^2$ and $W^2$ are as defined hereinbefore;

(e) reacting the latter compound with a deprotecting agent to obtain the corresponding amido acid of formula 7

$\text{A-N(R}^1\text{)C(O)CH}_2\text{CH(R}^2\text{)C(O)-OH}$     7 wherein A, $R^1$ and $R^2$ are as defined hereinbefore; and (f) coupling the latter amido acid with an amine of formula H-B wherein B is as defined hereinbefore; and, if required, eliminating any protective groups on the instant product used to protect competing reactive sites during the process, to obtain the corresponding compound of formula 1.

Note that with respect to the preceding compounds of formulae 2 to 7, inclusive, the aforementioned provisos regarding the stereochemistry of B and $R^2$ apply as well to the corresponding carbon atoms of these compounds.

Examples of suitable carboxy protective groups for the preceding processes are phenylmethoxy (benzyloxy), (4-nitrophenyl)methoxy, 9-fluorenylmethoxy and tert-butoxy. Note also that a 4-substituted-2-oxazolidinone group, arising from the use of an "Evans' chiral auxiliary" to prepare the monoprotected dicarboxylic acids 2 and 5, as described hereinafter, can be used as a carboxy protective group.

The requisite starting materials of formula 2 and formula 5 can be prepared by processes designed to give the desired stereochemistry. Convenient and practical processes for preparing the starting materials involve the application of the stereoselective alkylation method of D. A. Evans et al., J. Amer. Chem. Soc., 103, 2127 (1981) and J. Amer. Chem. Soc., 104, 1737 (1982). Such a process is illustrated by the following scheme directed to the preparation of the protected carboxylic acid 2 wherein $R^2$ is as defined herein, $W^1$ is tert-butoxy or phenylmethoxy (the carboxy protective group) and U is 1-methylethyl or benzyl.

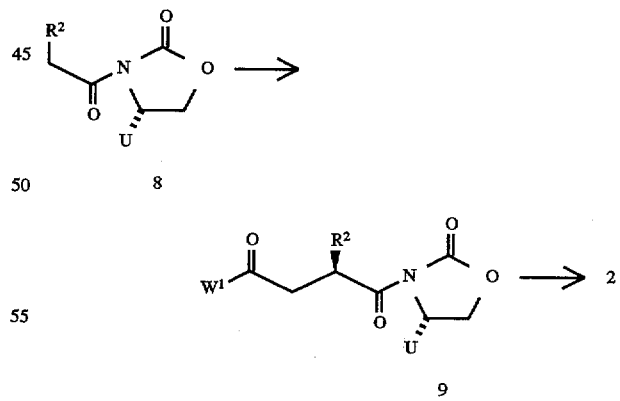

Accordingly, the chiral imide 8 is alkylated with tert-butyl α-bromoacetate or benzyl α-bromoacetate to afford the protected imide 9. Subsequent reaction of the latter compound with lithium hydroxide-hydrogen peroxide gives the monoprotected dicarboxylic acid of formula 2 in which $R^2$ and $W^1$ are as defined in the last instance.

In turn, the chiral imide 8 can be prepared by acylating the "Evans' chiral auxiliary", (S)-4-(1-methylethyl)-2- oxazolidinone or (S)-4-(phenylmethyl)-2-oxazolidinone, with the corresponding acid of formula $R^2CH_2COOH$ or a precursor acid capable of being transformed to the chiral imide 9.

An analogous process can be used to prepare the monoprotected dicarboxylic acids of formula 5. A convenient and practical process is realized for example by simply removing the carboxy protective group $W^1$ from the previously noted protected amide 9 whereby the desired monoprotected dicarboxylic acid of formula 5 is obtained. In this instance, the chiral auxiliary, i.e. the N-substituted 4(S)-(1-methylethyl)-2-oxazolidinone, assumes a new role as the carboxy protective group $W^2$.

Processes for preparing the monoprotected dicarboxylic acids of formulae 2 and 5 are illustrated in the examples hereinafter.

The amines of formula $ANH(R^1)$ in which A and $R^1$ are as defined herein are either known or can be prepared by standard methods for preparing amines, see for example S. G. Wilkinson in "Comprehensive Organic Chemistry, D. Barton and W. D. Ollis, Eds, Pergamon Press, Oxford, UK, Vol. 2, pp 3–302, 1979. Typical preparations of various amines of formula A-H are described in the examples.

The amines of formula H-B in which B is as defined hereinbefore are known, having been described by K. Nakano et al., European patent application 281 316, published Sep. 7, 1988, J. R. Luly et al., U.S. Pat. No. 4,845,079, issued Jul. 4, 1989, B. Quirico et al., European patent application 332 008, published Sep. 13, 1989, K. Hemmi et al., U.S. Pat. No. 4,963,530, issued Oct. 16, 1990, P. D. Williams et al., J. Med. Chem., 34, 887 (1991) and F. Matsuda et al., Bull. Chem. Soc. Jpn., 65, 360 (1992).

In the instance where a particular compound of formula 1 has a residue which functions as a base, the compound can be obtained in the form of a therapeutically acceptable acid addition salt. Examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In general, the therapeutically acceptable salts of the compounds of formula 1 are biologically fully equivalent to the peptides themselves.

Biological Aspects

The compounds of formula 1 possess the ability to inhibit renin activity. The renin inhibiting activity and enzyme specificity of the compounds can be demonstrated in standard pharmacological tests such as those described by J. R. Luly et al., Biochem. Biophys. Res. Comm., 143, 44 (1987).

In vitro renin inhibiting activity for the compounds has been demonstrated in the plasma renin assay, see example 6 hereinafter.

Primates (e.g. marmosets, cynomolgus monkeys and baboons) are a preferred species for demonstrating in vivo activity for renin inhibitors, because there is substantial homology in the sequence of primal& renin and human renin. In this connection, compounds of this invention have shown blood pressure lowering effects when the compounds were administered intravenously or orally to sodium-depleted cynomolgus monkeys, pretreated 18 hours before with an intramuscular injection (2.5 mg/kg) of furosemide to stimulate endogenous renin secretion.

Accordingly, the compounds are indicated for the diagnosis, prophylaxis and treatment of renin-associated hypertension in mammals including humans, primates, horses and dogs. The compounds also can be used for treating congestive heart failure in mammals including humans, primates, horses and dogs. For the latter purposes or indications, the compounds can be administered orally or parenterally in a vehicle comprising one or more pharmaceutically acceptable carriers, the proportion of which is determined by the solubility and chemical nature of the compounds, chosen route of administration and standard biological practice. For oral administration, the compound can be formulated in unit dosage forms such as capsules or tablets each containing a predetermined amount of the active ingredient, ranging from about 25 to 250 mg, in a pharmaceutically acceptable carrier.

For parenteral administration, the compound of formula 1 is administered by either intravenous, subcutaneous or intramuscular injection, in compositions with pharmaceutically acceptable vehicles or carriers. For administration by injection, it is preferred to use the compound in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations can be found in standard pharmaceutical texts, e.g. in "Remington's Pharmaceutical Sciences", 18th ed, Mack Publishing Company, Easton, Pa., 1990.

The dosage of the compound will vary with the form of administration and the particular active agent chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound is most desirably administered at a concentration level that will lower blood pressure without causing any harmful or deleterious side effects.

For oral administration, the compound is administered in the range of 1.0 to 50 mg per kilogram of body weight per day, with a preferred range of 1.0 to 30 mg per kilogram per day.

With reference to systemic administration, the compound of formula 1 is administered at a dosage of 0.1 mg to 5.0 mg per kilogram of body weight per day, although the aforementioned variations will occur. However, a dosage level that is in the range of from about 0.1 mg to 1.0 mg per kilogram of body weight per day is most desirably employed in order to achieve effective results.

The following examples illustrate further this invention. Temperatures are given in degrees Celsius. Solution percentages or ratios express a volume to volume relationship, unless stated otherwise. Nuclear magnetic resonance spectra were recorded on a Bruker 200 MHz or 400 MHz spectrometer (a 400 MHz spectrum being noted as such in the preamble of the spectrum); the chemical shifts (δ) are reported in parts per million. The concentrations for the optical rotations are expressed in grams of the compound per 100 mL of solution. Abbreviations or symbols used in the examples include Boc: t-butyloxycarbonyl; BOP-PF$_6$: (benzotriazol-1-yloxy)tris(dimethylamino)phosphonium hexafluorophosphate; Bzl: benzyl; $CH_2Cl_2$, methylenedichloride; DMAP: 4-(dimethylamino)-pyridine; DIPEA:

diisopropylethylamine; DMF: dimethylformamide; EtOH: ethanol; EtOAc: ethyl acetate; Et2O: diethyl ether; FAB/MS: fast atom bombardment mass spectrometry; HOBt: 1-hydroxybenzotriazole; MeOH: methanol; Ph: phenyl; TFA: trifluoroacetic acid; THF: tetrahydrofuran.

EXAMPLE 1

Typical Preparations of Amines of Formula A-H.

(a) (S)-N,N-Dimethyl-2-[(1-phenylethyl)amino]-acetamide: A mixture of 2-bromo-N,N-dimethylacetamide (5.71 g, 34.4 mmol), (S)-1-phenylethylamine (4.16 g, 34.4 mmol) and triethylamine (6.96 g, 68.8 mmol) in MeOH (69 mL) was stirred at room temperature (20°–22°) for 30 min and then heated at reflux for 30 min. The mixture was concentrated under reduced pressure. The residue was dissolved in EtOAc (400 mL). The solution was washed serially with a saturated aqueous solution of $NaHCO_3$ and brine, dried ($MgSO_4$) and concentrated to dryness under reduced pressure. The residue was purified by flash chromatography ($SiO_2$, eluent: $CHCl_3$-EtOH, 15:1) to give (S)-N,N-dimethyl-2-[(1-phenylethyl)amino]acetamide as a colorless oil (4.58 g, 64%); $^1H$ NMR($CDCl_3$) δ 7.36-7.17 (m,5H), 3.76 (q, J=7.1 Hz,1H), 3.24 (s,2H), 2.93 (s,3H), 2.80 (s,3H), 2.54 (broad s,1H), 1.39 (d, J=7.1 Hz,3H).

By following the procedure of section (a) of this example but replacing (S)-1-phenylethylamine with an equivalent amount of (S)-2-phenylpropylamine [described by H. Biere et al., J. Med. Chem., 17, 716 (1974)], (S)-N,N-dimethyl-2-[(2-phenylpropyl)amino]acetamide [$^1H$ NMR($CDCl_3$) δ 7.39-7.14 (m,5H), 3.37 ($q_{AB}$, Δv=12 Hz, J=14.3 Hz,2H), 3.07-2.68 (m,3H), 2.94 (s,3H), 2.90 (s,3H), 2.26 (broad s, 1H), 1.30 (d, J=6.5 Hz, 1H)] was obtained.

By following the procedure of section (a) of this example but replacing (S)-1-phenylethylamine with an equivalent amount of 2-phenylethylamine, N,N-dimethyl-2-[(2-phenylethyl)amino]acetamide [$^1H$ NMR($CDCl_3$) δ 7.37-7.14 (m,5H), 3.43 (s,2H), 2.96 (s,3H), 2.94 (s,3H), 2.91-2.82 (m,4H), 2.06 (broad s,1H)] was obtained.

By following the procedure of section (a) of this example but replacing (S)-1-phenylethylamine with an equivalent amount of (cyclohexylmethyl)amine, 2-[(cyclohexylmethyl)amino]-N,N-dimethylacetamide [$^1H$ NMR($CDCl_3$) δ 3.41 (s,2H), 2.97 (s,3H), 2.96 (s,3H), 2.44 (d, J=7.1 Hz,2H), 2.21 (broad s,1H), 1.86-0.82 (m, 1H)] was obtained.

By following the procedure of section (a) of this example but replacing (S)-1-phenylethylamine with twice the equivalent amount of (cyclohexylmethyl)amine and replacing 2-bromo-N,N-dimethylacetamide with an equivalent amount of 4-(2-bromo-1-oxoethyl)morpholine, 4-{2-[(cyclohexylmethyl)amino]-1-oxoethyl}morpholine [$^1H$ NMR($CDCl_3$) δ 3.76-3.54 (m,3H), 3.43-3.33 (m,4H), 2.45 (d, J=6.6 Hz,2H), 2.41 (broad s,1H), 1.84-0.84 (m, 11H)] was obtained.

By following the procedure of section (a) of this example but replacing (S)-1-phenylethylamine with twice the equivalent amount of 1-(naphthylmethyl)amine and omitting the triethylamine, N,N-dimethyl-2-[(1-naphthylmethyl)-amino] acetamide [$^1H$ NMR($CDCl_3$) δ 8.25 (dd, J=1.2 Hz,8.0 Hz,1H), 7.86 (dd, J=1.8 Hz,7.6 Hz,1H), 7.79 (broad d, J=8.1 Hz,1H), 7.60-7.39 (m,4H), 4.30 (s,2H), 3.52 (s,2H), 2.97 (s,3H), 2.90 (s,3H)] was obtained.

(b) N-[2-(methylamino)ethyl]-N-methylmorpholinocarboxamide: To a solution of N-(tert-butyloxycarbonyl)-N,N-dimethyl-1,2-ethanediamine (2.8 g, 14.9 mmol) in 50 mL of acetonitrile, DIPEA (3.6 mL, 20.7 mmol) and morpholinocarbonyl chloride (1.75 mL, 15.0 mmol) were added. The reaction mixture was stirred at room temperature for 1 h. Thereafter, EtOAc and a saturated aqueous solution of $NaHCO_3$ were added to the mixture. The organic layer was separated, washed with saturated aqueous brine, dried ($MgSO_4$) and concentrated to dryness under reduced pressure. The residue was purified by flash chromatography ($SiO_2$, eluent: EtOAc/hexane, 3:7) to give the corresponding Boc derivative of the desired amine as a white solid (3.18 g, 71%); $^1H$ NMR ($CDCl_3$) δ 3.68 (t, J=4.3 Hz, 4H), 3.39 (broad s, 4H), 3.20 (broad t, J=4.1 Hz, 4H), 2.93 (s,3H), 2.86 (s,3H), 1.45 (s,9H); FAB mass spectrum, m/z: 302 (M+H)$^+$, 324 (M+Na)$^+$.

The latter compound was deprotected as follows: A solution of the latter compound (1.0 g, 3.3 mmol) in 4 N HCl/dioxane (40 mL) was stirred at room temperature for 45 min. The mixture was concentrated to dryness. The residue was serially dissolved and the resulting solution concentrated, first with $Et_2O$ and then with toluene to afford N-[2-(methylamino)ethyl]-N-methylmorpholinocarboxamide as a hydrochloride addition salt (0.79 g). This amine hydrochloride salt was used for ensuing reactions without further purification.

(c) 4-[3-(methylamino)-1-oxopropyl]morpholine: A solution of 4-acryloylmorpholine (3.0 g, 21.25 mmol) in 4 mL of methylamine (40% solution in $H_2O$, 57.1 mmol) was heated at 40° for 4 days. Subsequently, the reaction mixture was concentrated to dryness and the residue was dissolved in $CHCl_2$ (10 mL). Triethylamine (3.7 mL, 26.5 mmol) and di-tert-butyl dicarbonate (4.6g, 21.10 mmol) were added to the solution. The reaction mixture was stirred at room temperature for 18 h. Thereafter, EtOAc and saturated aqueous $NaHCO_3$ were added to the mixture. The organic phase was separated, washed with saturated brine, dired ($MgSO_4$) and concentrated to dryness. The residue was purified by flash chromatography ($SiO_2$, eluent: MeOH/$CHCl_3$, 1:40) to give the corresponding Boc derivative of the desired amine as a colourless oil (1.88g, 32.5%); $^1H$ NMR ($CDCl_3$) δ (t, J=4.6 Hz, 4H), 3.59 (broad doublet, J=4.7 Hz, 2H), 3.49 (t, J=7.2 Hz, 4H), 2.87 (s,3H), 2.56 (m,2H), 1.44 (s,9H); FAB mass spectrum, m/z: 273 (M+H)$^+$, 295 (M+Na)$^+$.

The latter compound (0.743 g) was deprotected in the same manner as described in preceding section (b) to give 4-[3-(methylamino)-1-oxopropyl]morpholine as a hydrochloride addition salt (0.447g). This amine hydrochloride was used for ensuing reactions without further purification.

(d) 4-[2-(Methylamino)ethyl]morpholine: Under a $N_2$ atmosphere, NaH (1.0 g, 42.9 mmol, 97% dry powder) was added portionwise to a cooled solution (0°) of 4-(2-aminoethyl)morpholine (5.0 mL, 38.1 mmol) in dry THF (80 mL). The resulting mixture was treating with di-tert-butyl dicarbonate (8.4 g, 38.5 mmol) and stirred for 1 h. The NaH remaining in the mixture was decomposed by cautious dropwise addition of $H_2O$. After diluting the mixture with EtOAc and $H_2O$, the organic layer was separated, washed with brine, dried ($MgSO_4$), and concentrated under reduced pressure to give the corresponding Boc derivative of the starting material as a pale yellow oil (7.6 g, 88%); $^1H$ NMR ($CDCl_3$) 4.98 (broad s, 1H), 3.71 (t, J=4.6 Hz, 4H), 2.92 (m,2H), 2.46 (m,6H), 1.46 (s,9H); FAB mass spectrum, m/z: 231 (M+H)$^+$.

The latter oil (5.76 g, 25 mmol) was dissolved in dry THF (60 mL). Under a $N_2$ atmosphere at 0°, potassium bis (trimethylsilyl)amide (40 mL of 0.69 M solution in THF 27.6 mmol) was added to the solution. The mixture was stirred for 30 min. at room temperature. After an addition of methyl iodide (3 mL, 49 mmol), the reaction mixture was stirred for 1 h more. The reaction mixture was diluted with H$_2$O and EtOAc. The organic layer was separated, washed with brine, dried (MgSO$_4$) and concentrated under reduced pressure. Purification of the residue by flash chromatography (SiO$_2$, eluent: MeOH/CHCl$_3$, 1:40) gave the corresponding Boc derivative of the desired amine as a colourless oil (4.21g, 69%); $^1$H NMR (CDCl$_3$) δ 3.69 (t, J=4.5 Hz, 4H), 3.34 (m,2H), 2.87 (s,3H), 2.48 (m,6H), 1.46 (s 9H); FAB mass spectrum, m/z: 245 (M+H)$^+$, 267 (M+Na)$^+$.

The latter compound (0.5 g) was deprotected in the same manner as described in preceding section (b) to give 4-[2-(methylamino)ethyl)morpholine as a hydrochloric acid addition salt. The amine hydrochloride was used for ensuing reactions without further purification. (e) (S)-N-Methyl-2-[(1-phenylethyl)amino]-N-[2-(2-pyridinyl)ethyl]acetamide: A mixture of benzyl 2-bromoacetate (30.00 g, 0.131 mol), (S)-1-phenylethyl-amine (16.18 g, 0.134 mol) and triethylamine (26.50 g, 0.262 mol) in THF (300 mL) was stirred at room temperature for 6 h. H$_2$O (100 mL) was added and the THF removed under reduced pressure. EtOAc (600 mL) and a saturated aqueous solution of NaHCO$_3$ (200 mL) were added to the concentrate. The organic phase was washed serially with H$_2$O and brine, dried (MgSO$_4$) and concentrated under reduced pressure to give a colorless oil (31.42 g), i.e. the crude amino ester (Ph-(S)-CH(CH$_3$)-NHCH$_2$C(O)OBzl). The latter compound (31.00 g) was dissolved is CH$_2$CH$_2$ (300 mL). Di-tert-butyl dicarbonate (25.89 g, 0.119 mol) was added to the latter solution. The mixture was stirred at room temperature for 4 days; an additional amount of di-tert-butyl dicarbonate (3.0 g) being added to the mixture on the second day. Thereafter, the mixture was washed serially with 1N aqueous HCl (2X), H$_2$O (2X), a saturated aqueous solution of NaHCO$_3$ (2X) and brine, dried (MgSO$_4$) and concentrated under reduced pressure to give a colorless oil (48.00 g). The latter oil was dissolved in MeOH (575 mL) and 2N aqueous NaOH (172.8 mL, 0.346 mol) was added to the solution. The mixture was stirred at room temperature for 8 h. The mixture was concentrated under reduced pressure. The aqueous residual solution was diluted with H$_2$O and washed with CH$_2$Cl$_2$. The aqueous phase was rendered acidic by addition of solid citric acid (79.5g) and then extracted with EtOAc (2X). The organic phase was washed with brine, dried (MgSO$_4$) and concentrated under reduced pressure to give (S)-Ph-CH(CH$_3$)-N(Boc)-CH$_2$C(O)OH as a colorless oil (26.85 g, 73%).

To a solution of the latter acid (4.30 g, 15.40 mmol), N-methyl-2-(2-pyridinyl)ethanamine (2.09 g, 15.40 mmol) and DIPEA (8.05 mL, 46.20 mmol) in CH$_2$Cl$_2$ (45 mL), BOP.PF$_6$ (6.94 g, 15.70 mmol) was added. The reaction mixture was stirred at room temperature for 1.5 h. EtOAc was added. The resulting solution was washed serially with a saturated aqueous solution of NaHCO$_3$ (2X), H$_2$O (2X) and brine, dried (MgSO$_4$) and concentrated under reduced pressure. The residue was purified by flash chromatography (SiO$_2$, eluent: EtOAc-MeOH, 30:1) to give the Boc derivative of the desired compound as a light yellow solid (4.30 g, 70%).

A solution of the latter compound (14.60 g, 36.75 mmol) in dioxane-MeOH (40 mL/3 mL) and 4N HCl/dioxane (138 mL) was stirred at room temperature for 1 h. The reaction mixture was diluted with EtOAc (500 mL) and an aqueous solution of 22% w/w Na$_2$CO$_3$ (320 g) was slowly added. The organic phase was separated, washed with brine, dried (MgSO$_4$) and concentrated under reduced pressure to give (S)-N-methyl-2-[(1-phenylethyl)amino]-N-[2-(2-pyridinyl)-ethyl]acetamide as a pale yellow oil (10.50 g, 96%); $^1$H NMR(CDCl$_3$) δ (1.2:1.0 mixture of rotamers) 8.51, 8.40 (2 broad d, J~4.6, 4.6 Hz, 1H), 7.59, 7.53 (2 td, J=7.6, 1.9 and 7.6, 1.9 Hz, 1H), 7.34-7.22 (m,5H), 7.18, 6.96 (2d, J=7.6, 7.6 Hz, 1H), 7.14-7.06 (m, 1H), 3.82 (q, J=6.7 Hz, 0.5H), 3.77-3.67 (m,1.5H), 3.52 (t, J=7.3 Hz, 1H), 3.25, 3.17 (s, ABq, Δv=18.5 Hz, J=15.5 Hz, 2H), 3.22 (broad s, 1H), 2.99 (t, J=7.3 Hz, 1H), 2.91, 2.72 (2s,3H), 2.90-2.85 (m, 1H), 1.41, 1.36 (2d, J=6.7, 6.7 Hz, 3H). The latter amine was used for ensuing reactions without further purification.

The procedure of section (e) can be used generally to prepare many of the amines of formula A-H. For example, by following the latter procedure but replacing (S)-1-phenylethylamine with an equivalent amount of benzylamine, N-methyl-2-[(phenylmethyl)amino]-N-[2-(2-pyridinyl)ethyl]acetamide was obtained via the corresponding Boc derivative. The Boc derivative had the following NMR: $^1$H NMR(CDCl$_3$) δ 8.60 (d, J=5 Hz, 1H), 8.40 (m, 1H), 7.70-7.00 (m,7H), 4.55-4.52 and 4.48 (2s,2H), 3.90 (d, J=11 Hz, 1H), 3.80-3.55 (m,2H), 3.10-2.90 (m,3H), 2.90 (s,3H), 1.50 (3s,9H).

EXAMPLE 2

Preparation of N$^4$-[2-(Dimethylamino)-2-oxoethyl]-N$^4$-[1 (S)-phenylethyl ]-N$^1$-[1(S)-(cyclohexylmethyl)-2(R),3(S)-dihydroxy-5-methylhexyl ]-2(R)-[(2-amino-4-thiazolyl) methyl]butanediamide (a) 4-Bromo-4-pentenoic acid: tert-Butyl acetate (35 g, 301 mmol) was added dropwise to a stirred, freshly prepared solution of lithium diisopropylamine (319 mmol) in THF (800 mL) at −78°. The mixture was stirred for 25 min at −78°. Thereafter, 2,3-dibromo-1-propene (88.6 g, 443 mmol) was added to the mixture. Stirring was continued at −78° for an additional 4 h. The mixture was quenched at −78° with a saturated aqueous solution of NH$_4$Cl. The THF was removed under reduced pressure. The oily residue was dissolved in EtOAc. The organic layer was washed with a saturated aqueous solution of NH$_4$Cl (1X), H$_2$O (1X) and brine (2X), dried (MgSO$_4$) and concentrated. The residue was dissolved in a solution of TFA-CH$_2$Cl$_2$ (1:1, 500 mL) and the resulting solution was allowed to stand at room temperature for 1 h. The volatiles were removed by evaporation under reduced pressure. The residue was taken up in a saturated aqueous solution of NaHCO$_3$. The resulting solution was washed twice with CH$_2$Cl$_2$. The aqueous phase was rendered acidic with 1N aqueous HCl and extracted with EtOAc (2X). The EtOAc extract was washed with brine (1X), dried (MgSO$_4$) and evaporated to dryness to give 4-bromo-4-pentenoic acid (39.7 g, 74%); $^1$H NMR (CDCl$_3$) δ 11.45 (broad s,1H), 6.13 (d, J=2.9 Hz,1H), 5.93 (d, J=2.9 Hz,1H), 3.40-3.05 (m,4H).

(b) 3-(4-Bromo-1-oxo-4-pentenyl)-4(S)-(1-methylethyl)-2-oxazolidinone: A solution of mixed anhydride was prepared by adding, under N$_2$, pivaloyl chloride (253 μL, 2.06 mmol) to a stirred solution of 4-bromo-4-pentenoic acid (350 mg, 1.96 mmol) and triethylamine (332 μL, 2.38 mmol) in dry THF (3.3 mL) cooled to −78°. The mixture was warmed to 0°, stirred for 1 h and then cooled to −78°. Another solution was prepared by adding dropwise under N$_2$ a 1.6M hexane solution of butyllithium (1.1 mL, 1.79 mmol) to a cooled solution (−45° to −50°) of (S)-4-(1-methylethyl)-2-oxazolidinone [230 mg, 1.79 mmol, described by L. N. Pridgen et al., J. Org. Chem., 54, 3231 (1989)] in dry THF (8.9 mL). The latter solution was cooled to −78° and then added rapidly, via cannulation, to the stirred solution of the mixed anhydride, noted previously. The resulting mixture was stirred at −78° for 2 h. After warming to 0°, the mixture was partitioned between $CH_2Cl_2$ and phosphate buffer (pH 7). The $CH_2Cl_2$ layer was separated, washed with a saturated aqueous solution of $NaHCO_3$ (1X) and brine (1X), dried ($MgSO_4$) and evaporated to dryness under reduced pressure. The residual oil was purified by flash chromatography ($SiO_2$, eluent: EtOAc-hexane, 1:9) to give the desired 2-oxazolidinone derivative as a colorless oil (354 mg, 69%); $^1$H NMR ($CDCl_3$) δ 5.67 (d, J=2.9 Hz,1H), 5.54 (d, J=2.9 Hz,1H), 4.50-4.35 (m, 1H), 4.35-4.15 (m,2H), 3.35-3.05 (m,2H), 2.90-2.70 (m,2H), 2.50 (hept d, J=3.8 Hz,8.6 Hz,1H), 0.93 (d, J=8.6 Hz,3H), 0.87 (d, J=8.6 Hz,3H).

(c) 3-(5-Bromo-1,4-dioxopentyl)-4(S)-(1-methylethyl)-2-oxazolidinone: Recrystallized N-bromosuccinimide (960 mg, 5.39 mmol) was added to a cold (0°) stirred solution of the 2-oxazolidinone derivative of section (b) of this example (311.6 mg, 1.08 mmol) in acetonitrile (10 mL) and $H_2O$ (485 µL, 27.0 mmol). The resulting orange mixture was stirred at 0° for 30 min and then allowed to warm to room temperature. After 1 h the reaction mixture was quenched with a 10% (w/v) aqueous solution of $Na_2S_2O_3$ and extracted with EtOAc. The EtOAc extract was washed serially with $H_2O$, 10% (w/v) aqueous $Na_2S_2O_3$, $H_2O$ and brine. Drying ($MgSO_4$) and concentration of the extract afforded a yellow oil. The oil was purified by flash chromatography ($SiO_2$, eluent: EtOAc-hexane, 3:7) to give the bromoketone, 3-(5-bromo-1,4-dioxopentyl)-4(S)-(1-methylethyl)-2-oxazolidinone, as a colorless oil (320 mg, 97%); NMR ($CDCl_3$) δ 4.50-4.35 (m, 1H), 4.35-4.15 (m,2H), 4.01 (s,2H), 3.35-3.20 (m,2H), 3.05-2.90 (m,2H), 2.33 (hept d, J=3.7 Hz,7.0 Hz,1H), 0.91 (d, J=7.0 Hz,3H), 0.87 (d, J=7.0 Hz,3H).

(d) 3-[3-(2-Amino-4-thiazolyl)-1-oxopropyl]-4(S)-(1-methylethyl)-2-oxazolidinone: Thiourea (312 mg, 4.10 mmol) was added to a solution of the bromoketone of section (c) of this example (250 mg, 0.82 mmol) in isopropanol (8.2 mL). The mixture was stirred at 50° for 20 min, cooled and evaporated to dryness under reduced pressure. The residue was dissolved in EtOAc. The EtOAc solution was washed with an saturated aqueous solution of $NaHCO_3$ (2X), $H_2O$ (2X) and brine (1X), dried ($MgSO_4$) and evaporated to dryness to give the desired aminothiazolyl derivative as a solid (197 mg, 85%); $^1$H NMR ($CDCl_3$) δ 6.16 (s,1H), 5.37 (broad s,2H), 4.55-4.35 (m, 1H), 4.35-4.15 (m,2H), 3.45-3.10 (m,2H), 3.05-2.80 (m,2H), 2.35 (hept d, J=3.8 Hz,7.0 Hz,1H), 0.90 (d, J=7.0 Hz,3H), 0.85 (d, J=7.0 Hz,3H). The product was used for the next step without further purification.

(e) 4(S)-(1-Methylethyl)-3-{3-{2-[(2,2,2-trichloroethoxy) carbonylamino]-4-thiazolyl}-1-oxopropyl}-2-oxazolidinone: 2,2,2-Trichloroethyl chloroformate (171 µL, 1.24 mmol) was added to a solution of the aminothiazolyl derivative of section (d) of this example (185 mg, 0.65 mmol), DIPEA (205 µL, 1.18 mmol) and DMAP (8 mg, 0.07 mmol) in $CH_2Cl_2$ (3.3 mL) at room temperature. The reaction mixture was stirred at room temperature for 1 h. Thereafter, the mixture was diluted with EtOAc, washed serially with a saturated aqueous solution of $NaHCO_3$ (2X), $H_2O$ (3X) and brine (2X), dried ($MgSO_4$) and evaporated to dryness. The residue was purified by flash chromatography ($SiO_2$, eluent: EtOAc-hexane, 3:7) to give the desired product (250 mg, 84%); $^1$H NMR (400 MHz, $CDCl_3$) δ 10.27 (broad s,1H), 6.64 (s,1H), 4.93 ($q_{AB}$ $J_{AB}$=12.0 Hz,2H), 4.48-4.38 (m, 1H), 4.32-4.18 (m,2H), 3.45-3.20 (m,2H), 3.20-3.05 (m,2H), 2.36 (hept d, J=3.8 Hz,7.0Hz,1H), 0.91 (d, J=7.0 Hz,3H), 0.86 (d, J=7.0 Hz,3H); FAB mass spectrum, m/z: 458 (M+H)$^+$, 480 (M+Na)$^+$.

(f) 3-{4-tert-Butoxy-4-oxo-2(R)-{{2-[(2,2,2-trichloroethoxy) carbonylamino]-4-thiazolyl}methyl}-butyl}-4-(S)-(1-methylethyl)-2-oxazolidinone: A solution of the product of section (e) of this example (615 mg, 1.35 mmol) in THF (5.0 mL) was added to a cold (−78°) solution of sodium bis-(trimethylsilyl)amide (3.1 mL, 3.1 mmol) in THF (3.0 mL). [Sodium bis(trimethylsilyl)amide is supplied as a 1M solution in THF by the Aldrich Chemical Co., Inc., Milwaukee, Wis., USA.] The mixture was stirred at −78° for 40 min. A solution of tert-butyl 2-bromoacetate (435 µL, 2.69 mmol) in THF (1 mL) was added to the mixture which was then stirred at −78° for 1.5 h. The mixture was quenched with a saturated aqueous solution of $NH_4Cl$ and diluted with EtOAc. The organic phase was separated, washed with $H_2O$ and brine, dried ($MgSO_4$) and evaporated. The residue was purified by flash chromatography ($SiO_2$, eluent: EtOAc-hexane, 1:4) to give the desired tert-butyl ester derivative (459 mg, 60%); $^1$H NMR (400 MHz, $CDCl_3$) δ 10,.50 (broad s,1H), 6.70 (s,1H), 4.92 ($q_{AB}$, $J_{AB}$=12.1 Hz,2H), 4.55-4.40 (m, 1H), 4.40-4.30 (m, 1H), 4.20-4.05 (m,2H), 3.10-2.90 (m,2H), 2.85-2.65 (m, 1H), 2.47-2.38 (m, 1H), 2.32 (hept d, J=3.8 Hz,7.0 Hz,1H), 1.39 (s,9H), 0.89 (d, J=7.0 Hz,3H), 0.87 (d, J=7.0 Hz,3H); FAB mass spectrum, m/z: 572 (M+H)$^+$.

(g) The protected amido acid, 4-{[1(S)-(cyclohexylmethyl)-2(R),3(S)-dihydroxy-5-methylhexyl]amino}-4-oxo-3-(R)-{{2-[(2,2,2-trichloroethoxy) carbonylamino]-4-thiazolyl}methyl}butanoic acid tert-butyl ester: A solution of the product of section (f) of this example (57.5 mg, 0.10 mmol) in THF (1.5 mL) and $H_2O$ (0.5 mL) was cooled to 0°. A 30% aqueous solution of $H_2O_2$ (91.3 µL, 0.80 mmol of $H_2O_2$) and lithium hydroxide monohydrate (8.5 mg, 0.20 mmol) were added serially to the cooled solution. The mixture was stirred at 0° for 5 min and then at room temperature for 2.5 h. Excess $H_2O_2$ was quenched by the addition of a 1.5M aqueous solution of $Na_2SO_3$ (as judged by a KI stick indicator). The resulting mixture was diluted with $H_2O$ and washed with $CH_2Cl_2$ (3X). The aqueous layer was rendered acidic with 1N aqueous HCl and extracted with EtOAc (3X). The combined EtOAc extracts were washed with brine, dried ($MgSO_4$) and concentrated to dryness to yield the desired monoprotected dicarboxylic acid, i.e. the 4-tert-butyl ester of 2(R)-{{2-[(2,2,2-trichloroethoxy) carbonylamino]-4-thiazolyl}-methyl}-butanedioic acid. The monoprotected dicarboxylic acid was used for the following coupling step without purification.

The monoprotected dicarboxylic acid (0.10 mmol) was dissolved in DMF (1 mL). DIPEA (43.8 µL, 0.25 mmol), BOP.PF$_6$ (48 mg, 0.11 mmol) and 2(S)-amino-1-cyclohexyl-6-methyl-3 (R),4(S)-heptanediol hydrochloride (30 mg, 0.11 mmol) were added to the solution. The pH of the mixture was adjusted to pH 8.5 with DIPEA. The resulting mixture was stirred at room temperature for 2.5 h. Thereafter, the mixture was diluted with EtOAc. The organic phase was washed with 1N aqueous HCl, a saturated aqueous solution of $NaHCO_3$, $H_2O$ and brine, dried ($MgSO_4$) and evaporated to dryness. The residue was purified by flash chromatography ($SiO_2$, eluent: EtOAc-hexane, 3:7) to give desired protected amide (27.9 mg, 40%); $^1$H NMR (400 MHz, $CDCl_3$) δ 10.23 (broad s,1H), 6.66-6.59 (m,2H), 4.85 ($q_{AB}$, $J_{AB}$=11.8 Hz,2H), 4.55-4.40 (m, 1H), 4.30-4.15 (m, 1H), 3.55-3.43 (m, 1H), 3.35-3.05 (m,3H), 3.05-2.85 (m, 1H), 2.80-2.65 (m, 1H), 2.43-2.33 (m, 1H), 2.00-1.80 (m, 1H), 1.80-1.70 (m, 1H), 1.70-1.00 (m, 11H), 1.44 (s,9H), 1.00-0.70 (m,3H), 0.94 (d, J=6.6 Hz,3H), 0.85 (d, J=6.6 Hz,3H).

(h) The title compound: The preceding protected amido acid (190 mg, 0.28 mmol) was dissolved in a solution of TFA-$CH_2Cl_2$ (1:1, 5 mL) and the resulting solution was allowed to stand at room temperature for 1 h. The solution was evaporated to dryness. The residue was dissolved in DMF (2 mL). DIPEA (97 μL, 055 mmol), BOP.PF$_6$ (159 mg, 0.36 mmol) and (S)-N,N-dimethyl-2-[(1-phenylethyl) amino]acetamide [74 mg, 0.36 mmol, described in example 1, section (a)] were added serially to the DMF solution. The pH of the solution was adjusted to 8.5 with DIPEA. Thereafter, the reaction mixture was stirred at room temperature for 18 h. The mixture was diluted with EtOAc. The organic phase was washed with 1N aqueous HCl (1X), a saturated aqueous solution of NaHCO$_3$ (2X), brine (2X), dried (MgSO$_4$) and concentrated to dryness. The residue was purified by flash chromatography (SiO$_2$, eluent: hexane-EtOAc-MeOH, 100:97:3) to give the corresponding N-{2-[(2,2,2-trichloroethoxy)carbonyl]} derivative of the title compound as a yellow oil (84 mg, 37%); $^1$H NMR (400 MHz, CDCl$_3$) (ca 1.5:1 mixture of isomers) δ 9.80 (s,1H), 7.40-7.20 (m,5H), 6.84 and 6.75 (2d, J=8.8 Hz,8.8 Hz,1H), 6.78 and 6.63 (2s,1H), 6.10 and 5.15 (2q, J=6.9 Hz,6.9 Hz,1H), 4.85 (q$_{AB}$, J$_{AB}$=11.9 Hz,2H), 4.46-4.18 (m,2H), 3.85-3.05 (m,5H), 3.05-2.40 (m,4H), 2.92, 2.87, 2.91 and 2.80 (4s,6H), 2.00-1.80 (m, 1H), 1.80-1.05 (m,14H), 1.56 and 1.40 (2d,6.9 Hz,6.9 Hz,3H), 1.05-0.75 (m,2H), 0.93 (d, J=6.6 Hz,3H), 0.84 (d, J=6.6 Hz,3H); FAB mass spectrum, m/z: 820 (M+H)$^+$, 644 (M - C$_2$H$_2$O$_2$Cl$_3$)$^+$; [α]$^{25}_D$ −45.6° (c 1.00, MeOH). The (2,2,2-trichloroethoxy)carbonyl protective group of the latter derivative was eliminated as follows: The latter derivative (645 mg, 0.79 mmol) was dissolved in 1N aqueous HCl/dioxane (1:2, 6 mL). Zinc metal powder (6.45 g) was added to the solution. The mixture was sonicated at room temperature for 4.5 h. A saturated aqueous solution of NaHCO$_3$ was added. The suspended zinc salt was collected on a filter and washed several times with EtOAc. The organic phase in the filtrate was separated and washed with a saturated aqueous solution of NaHCO$_3$ (2X), brine (2X), dried (MgSO$_4$) and evaporated to dryness. The residue was purified by flash chromatography (SiO$_2$, eluent: MeOH-EtOAc, 3:97) to give the title compound as a white solid (438 mg, 86%); $^1$H NMR (400 MHz, CDCl$_3$) (ca 1.5:1 mixture of rotamers) δ 7.38-7.22 (m,5H), 6.77 and 6.64 (2d, J=8.5 Hz,8.5 Hz,1H), 6.27 and 6.23 (2s,1H), 6.05 and 5.18 (q, J=6.6 Hz,6.6Hz,1H), 5.40-5.25 (m,2H), 4.65-4.45 (m, 1H), 4.45-4.18 (m, 1H), 3.85-3.70 (m, 1H), 3.70-3.40 (m, 1H), 3.40-3.10 (m,3H), 3.10-2.50 (m,5H), 2.94, 2.88, 2.91 and 2.83 (4s,6H), 2.00-1.85 (m, 1H), 1.85-1.73 (m, 1H), 1.59 and 1.38 (2d, J=6.8 Hz,6.8 Hz,3H,rotamers), 1.73-1.05 (m,12H), 0.93 (d, J=6.71 Hz,3H), 0.85 (d, J=6.7 Hz,3H), 1.00-0.75 (m,2H); FAB mass spectrum, m/z: 644 (M+H)$^+$, 628 (M - Me)$^+$; [α]$^{25}_D$ −58.8° (c 1.00, MeOH).

Alternatively, the title compound was prepared as follows:

3-{4-tert-Butoxy-4-oxo-2(R)-{{2-[(2,2,2-trichloroethoxy)carbonylamino ]-4-thiazolyl}methyl}butyl}-4(S)-(1-methylethyl)-2-oxazolidinone (5.78 g, 10.1 mmol), i.e. the product of section (f) of this example), was dissolved in a solution of TFA-CH$_2$Cl$_2$ (1:1, 50 mL). The solution was stirred at 0° for 1 h and then at room temperature for 2.5 h. Thereafter, the solution was evaporated to dryness. The residue was dissolved in DMF (51 mL). DIPEA (2.1 mL, 12.2 mmol), BOP.PF$_6$ (5.37 g, 12.2 mmol) and (S)-N,N-dimethyl-2-[(1-phenylethyl)amino]acetamide (2.40 g, 11.6 mmol) were added serially to the DMF solution at 0°. The pH of the solution was adjusted to 8.5 with DIPEA. The reaction mixture was stirred at 0° for 30 min and then at room temperature for 3.5 h. The mixture was diluted with EtOAc. The organic phase was washed with 1N aqueous HCl (1X), a saturated aqueous solution of NaHCO$_3$ (2X), brine (2X), dried (MgSO$_4$) and concentrated to dryness. The residue was purified by flash chromatography (SiO$_2$, eluent: hexane-CHCl$_3$-MeOH, 5.5:3.5:1) to give the desired chiral acyloxazolidinone synthon of 4-{[2-dimethylamino)-2-oxoethyl)] -[1(S)-phenylethyl]-amino}-4-oxo-2(R)-{{2-[(2,2,2-trichloroethoxy)carbonylamino]-4-thiazoly}methyl}butanoic acid (4.84 g, 68%).

The chiral acyloxazolidinone synthon was transformed to the desired synthon as follows: A solution of the chiral acyloxazolidinone synthon (4.22 g, 6.0 mmol) in THF (90 mL) and H$_2$O (30 mL) was cooled to 0°. A 30% aqueous solution of H$_2$O$_2$ (4.9 mL, 48.0 mmol of H$_2$O$_2$) and lithium hydroxide monohydrate (504 mg, 12.0 mmol) were added serially to the cooled solution. The mixture was stirred at 0° for 30 min and then at room temperature for 2.5 h. Excess H$_2$O$_2$ was quenched by the addition of solid Na$_2$SO$_3$. The resulting mixture was diluted with water and rendered acidic with 1N aqueous HCl and extracted with EtOAc (3X). The combined EtOAc extracts were washed with 1N aqueous HCl (1X), brine (2X), dried (MgSO$_4$) and concentrated to dryness to yield the desired amido acid, i.e. 4-{[2-(dimethylamino)-2-oxoethyl)]-[1(S)-phenylethyl]-amino}-4-oxo-2(R)-{{2-[(2,2,2-trichloroethoxy)carbonylamino]-4-thiazoly}methyl}butanoic acid. The amido acid was used for the following coupling step without purification.

The preceding amido acid (6.0 mmol) was dissolved in DMF (48 mL). DIPEA (1.6 mL, 9.0 mmol) and BOP-PF$_6$ (3.2 g, 7.2 mmol) were added to the solution. The resulting mixture was stirred at 0° for 30 min. Thereafter, 2(S)-amino-1-cyclohexyl-6-methyl-3(R), 4(S)-heptanediol hydrochloride (2.0 g, 7.2 mmol) was added to the cooled solution. The pH of the solution was adjusted to 8.5 with DIPEA. The mixture was allowed to warm to room temperature over a period of 4.5 h. The mixture was diluted with EtOAc (1L). The organic phase was washed with 1N aqueous HCl (1X), a saturated aqueous solution of NaHCO$_3$ (2X), brine (2X), dried (MgSO$_4$) and evaporated to dryness. The residue was purified by flash chromatography (SiO$_2$, eluent: EtOAc-hexane-EtOH, 6:3:1) to give, after trituration with hexane/Et$_2$O (1:1), the N-{2-[(2,2,2-trichloroethoxy)carbonyl]} derivative of the title compound of this example (3.2 g, 65%), identical to the corresponding derivative of section (h) of this example. The (2,2,2-trichloroethoxy)carbonyl protective group of the latter derivative was removed in the same manner as described in section (h) to give the title compound.

EXAMPLE 3

Preparation of N$^4$-[2-(Dimethylamino)-2-oxoethyl]-N$^4$-[1(S)-phenylethyl]-N $^1$-[1(S)-(cyclohexylmethyl)-2(R),3(S)-dihydroxy-5-methylhexyl ]-2(R)-(1H-imidazol-4-ylmethyl) butanediamide (a) 1-(Triphenylmethyl)-1H-imidazole-4-propanoic acid: Triethylamine (26.73 g, 36.8 mL, 0.26 mol) was added dropwise to a solution of 1H-imidazole-4-propanoic acid methyl ester [32.58 g, 0.21 mol, described by J. Altman et al., J. Chem. Soc., Perkin Trans. 1, 59 (1984)] and triphenylmethyl chloride (64.80 g, 0.23 mol) in CH$_2$Cl$_2$ at room temperature. The mixture was stirred at room temperature for 63 h, diluted with CH$_2$Cl$_2$ (total volume=900 mL), washed with H$_2$O (2X), a saturated aqueous solution of NaHCO$_3$ (1X) and brine (1X), dried (MgSO$_4$) and concentrated to dryness under reduced pressure. The residue was dissolved in a mixture of THF/H$_2$O (630 mL: 210 mL). Lithium hydroxide monohydrate (22.03 g, 0.52 mol) was added to the solution. The mixture was stirred at room temperature for 3 h. Most of the THF was removed by distillation under reduced pressure. The residue was poured into H$_2$O (1 L). The pH of the resulting mixture was adjusted to 2 by the addition of 10% (w/v) aqueous citric acid. The mixture was extracted with CH$_2$Cl$_2$ (3X). The CH$_2$Cl$_2$ extract was washed with 10% (w/v) aqueous citric acid and brine, dried (MgSO$_4$) and concentrated under reduced pressure. The residue was triturated with Et$_2$O to give the desired acid as a white solid (77.14 g, 96%); $^1$H NMR (CDCl$_3$) δ 7.67 (d, J=1.5 Hz,1H), 7.41-7.34 (m,9H), 7.13-7.08 (m,6H), 6.66 (d, J=1.5 Hz,1H), 2.95-2.88 (m,2H), 2.82-2.76 (m,2H).

(b) 4(S)-(1-Methylethyl)-3-{1-oxo-3-[1-(triphenylmethyl)-1 H-imidazol-4-yl]propyl}-2-oxazolidinone: By following the procedure of example 2, section (b) and using the product of section (a) of this example (11.5 g, 30.1 mmol) to prepare the corresponding mixed anhydride which in turn is reacted with the (S)-4-(1-methylethyl)-2-oxazolidinone (3.53 g, 27.3 mmol), the desired product was obtained as a pale yellow solid (11.38 g, 84%); $^1$H NMR(CDCl$_3$) δ 7.36-7.29 (m, 10H), 7.17-7.10 (m,6H), 6.58 (d, J=0.7 Hz,1H), 4.40 (td, J=3.8 Hz, 7.5 Hz,1H), 4.29-4.14 (m,2H), 3.32-3.23 (m,2H), 2.96-2.88 (m,2H), 2.33 (hept d, J=3.8 Hz, 6.9Hz, 1H), 0.89 (d, J=7.0Hz, 3H), 0.82 (d, J=6.9 Hz,3H).

(c) 3-{1,4-Dioxo-4-(phenylmethoxy)-2(R)-{[1-(triphenylmethyl)-1 H-imidazol-4-yl]methyl}butyl}-4-(S)-(1-methylethyl)-2-oxazolidinone: By following the procedure of example 2, section (f), but replacing the product of section (e) of that example with 4(S)-(1-methylethyl)-3-{1-oxo-3-[1-(triphenylmethyl)-1 H-imidazol-4-yl]propyl}-2-oxazolidinone of section (b) of this example, and replacing tert-butyl 2-bromoacetate with benzyl 2-bromoacetate, 3-{1,4-dioxo-4-(phenylmethoxy)-2-{[1-(triphenylmethyl)-1H-imidazol-4-yl]methyl}butyl}-4-(S)-(1 -methylethyl)-2-oxazolidinone was obtained as a mixture of 2(R)- and 2(S)-epimers in a 8 to 1 ratio by weight. Separation of the epimers by flash chromatography (SiO$_2$, eluent: hexane-EtOAc, 1:2) yielded the desired 2(R)-epimer (Rf=0.25, eluent: hexane-EtOAc,1:2). The $^1$H NMR(CDCl$_3$) of the 2(R)-epimer showed δ 7.34-7.28 (m, 15H), 7.13-7.08 (m,6H), 6.59 (d, J=1.3 Hz,1H), 5.06 (s,2H), 4.55-4.45 (m, 1H), 4.38 (td, J=3.9 Hz,5.4 Hz,1H), 4.15-4.10 (m,2H), 2.97 (dd, J=10.3 Hz,16.9 Hz,1H), 2.88 (dd, J=6.3 Hz,14.3 Hz,1H), 2.73 (dd, J=7.0 Hz,14.3 Hz,1H), 2.59 (dd, J=4.4 Hz,16.9 Hz,1H), 2.32 (hept d, J=3.9 Hz,7.0 Hz,1H), 0.87 (d, J=7.1 Hz,3H), 0.85 (d, J=6.8 Hz,3H).

(d) 4-{[1(S)-(Cyclohexylmethyl)-2(R),3(S)-dihydroxy-5-methylhexyl]amino}-4-oxo-3-{[(1-(triphenylmethyl)-1H-imidazol-4-yl]methyl}butanoic acid benzyl ester: A 30% aqueous solution of H$_2$O$_2$ (4.70 mL, 41.6 mmol) and lithium hydroxide monohydrate (436 mg, 10.4 mmol) were added serially to cooled solution (0°) of the product of section (c) of this example (6.67 g, 10.4 mmol) in THF-H$_2$O (156 mL: 52 mL). The reaction mixture was stirred at 0° for 2 h and then at room temperature for 2 h. Excess peroxide was quenched at 0° with 1.5N aqueous Na$_2$SO$_3$ solution. THF was removed by distillation under reduced pressure. The concentrate was poured into H$_2$O (500 mL). The mixture was rendered acid by the addition of a 10% (w/v) aqueous solution of citric acid, and then extracted with EtOAc. The extract was washed with brine, dried (MgSO$_4$) and evaporated to dryness under reduced pressure to yield the desired monoprotected dicarboxylic acid, i.e. the 4-(phenylmethyl) ester of 2(R)-{[1-(triphenylmethyl)-1H-imidazol-4-yl]methyl}butanedioiic acid. The monoprotected dicarboxylic acid was used for the following coupling step without further purification.

2(S)-Amino-1-cyclohexyl-6-methyl-3(R),4(S)-heptanediol hydrochloride (2.91 g, 10.4 mmol), DIPEA (3.62 g, 28.0 mmol) and BOP·PF$_6$ (4.82 g, 10.9 mmol) were added to a cooled (0°) solution of the preceding monoprotected dicarboxylic acid in DMF (42 mL). The mixture was stirred at room temperature for 6 h. Thereafter, the mixture was diluted with EtOAc. The organic phase was washed with a 10% (w/v) aqueous solution of citric acid (2X), H$_2$O (1X), a saturated aqueous solution of NaHCO$_3$ and brine, dried (MgSO$_4$) and concentrated to dryness under reduced pressure. The residue was purified by flash chromatography (SiO$_2$, eluent: hexane-isopropanol, 8:1) to give the desired protected amido acid as a white solid (6.08 g, 77%); $^1$H NMR (CDCl$_3$) δ 7.42 (d, J=1.2 Hz,1H), 7.37-7.30 (m,14H), 7.12-7.05 (m,6H), 6.54 (d, J=1.2 Hz,1H), 6.45 (broad d, J=9.6 Hz,1H), 5.11 (d, J=12.3 Hz,1H), 5.06 (d, J=12.3 Hz,1H), 4.43-4.38 (m, 1H), 3.30-2.64 (m,6H), 2.37 (dd, J=4.8 Hz,15.6 Hz,1H), 1.92-0.73 (m,16H), 0.87 (d, J=6.6 Hz,3H), 0.69 (d, J=6.5 Hz,3H).

(e) N$^1$-[1(S)-(Cyclohexylmethyl)-2(R),3(S)-dihydroxy-5-methylhexyl ]-N$^4$-[2-(dimethylamino)-2-oxoethyl]-N$^4$-[1(S)-phenylethyl ]-2(R)-{[1-(triphenylmethyl)1Himidazol-4-yl]methyl}butanediamide: A mixture of the protected amido acid of section (d) of this example (6.08 g, 8.04 mmol) and 10% palladium on carbon (600 mg) in EtOH (80 mL) was stirred under one atmosphere of hydrogen for 2.5 h. The mixture was filtered and the filtrate was concentrated to dryness under reduced pressure to give the desired amido acid, i.e. 4-{[1(S)-(cyclohexylmethyl)-2(R), 3(S)-dihydroxy-5-methylhexyl]amino}-3(R)-{[1-triphenylmethyl)-1H-imidazol-4-yl]methyl}-4-oxobutanoic acid, as a white solid (5.30 g, 99%). Without further purification, the latter amido acid was dissolved in DMF (32 mL) and cooled to 0°. (S)-N,N-dimethyl-2-[(1-phenylethyl)amino]acetamide [1.66 g, 8.07 mmol, described in example 1, section (a)], DIPEA (1.42 g, 10.98 mmol) and BOP·PF$_6$ (3.00 g, 6.78 mmol) were added to the cooled solution. The reaction mixture was stirred at 0° for 15 min and then at room temperature for 5 h. Thereafter, the mixture was diluted with EtOAc, washed successively with a 10% (w/v) aqueous solution of citric acid, H$_2$O, a saturated aqueous solution of NaHCO$_3$ and brine, dried (MgSO$_4$) and concentrated to dryness under reduced pressure. The residue was purified by flash chromatography (SiO$_2$, eluent: EtOAc-MeOH, 10:1) to give the desired product as a yellow solid (3.60 g, 65%); $^1$H NMR (CDCl$_3$) (ca 1:1 mixture of rotamers) δ 7.46 and 7.23 (2d, J=1.1 Hz,1.1 Hz,1H), 7.40-7.20 (m,14H), 7.15-7.00 (m,6H), 6.84-6.69 (m, 1H), 6.71 and 6.64 (2d, J=1.1 Hz,1.1 Hz,1H), 6.01 and 5.19 (2q, J=6.9 Hz,6.9 Hz,1H), 4.48-4.18 (m, 1H), 4.33, 3.14 and 3.84 (2d and q$_{AB}$, Δν=21.5 Hz, J=16.2 Hz,16.2 Hz,17.8 Hz,2H), 3.42-2.57 (m,7H), 2.96, 2.88, 2.87 and 2.82 (4s,6H), 1.96-1.03 (m,16H), 1.56 and 1.35 (2d, J=6.9 Hz,6.9 Hz,3H), 0.89, 0.88, 0.83 and 0.74 (4d, J=6.6 Hz,6.7 Hz,6.5 Hz,6.5 Hz,6H).

(f) The title compound: A mixture of the product of section (e) of this example (3.60 g, 4.21 mmol) and 10% (w/w) palladium hydroxide on carbon (1.44 g) in EtOH (50 mL) was shaken under an hydrogen atmosphere (50 psi) on a Parr hydrogenation apparatus for 2 days. The mixture was filtered. The filtrate was concentrated under reduced pressure. The residue was purified by flash chromatography (SiO$_2$, eluent: EtOAc-MeOH, 10:1) to give the title compound as a white solid; $^1$H NMR [(CD$_3$)$_2$SO] (1.5:1.0 mixture of rotamers) δ 7.72 and 7.61 (2d, J=8.4 Hz,8.8 Hz,1H), 7.54 and 7.50 (2 broad s,1H), 7.41-7.21 (m,5H), 6.83 and 6.77 (2 broad s,1H), 5.76 and 5.15 (2q, J=7.2 Hz,6.8 Hz,1H), 4.24, 4.12, 3.78 and 3.43 (4d, J=16.1

Hz,18.0 Hz,18.0 Hz,16.1 Hz,2H), 4.08 (broad s,1H), 3.20-2.95 (m,2H), 2.94-2.68 (m,2H), 2.87, 2.82, 2.77 and 2.74 (4s,6H), 2.67-2.46 (m,2H), 2.34 (d, J=6.9 Hz,1H), 1.83-0.98 (m, 16H), 1.45 and 1.31 (2d, J=6.8 Hz and 7.2 Hz,3H), 0.84 (d, J=6.6 Hz,3H), 0.72 (d, J=6.4 Hz,3H); FAB mass spectrum, m/z: 612 (M+H)$^+$, 634 (M+Na)$^+$; $[\alpha]^{25}_D$ –59.1° (c 1.02 MeOH).

EXAMPLE 4

Preparation of N$^4$-[2-(Dimethylamino)-2-oxoethyl]-N$^4$-[1 (S)-phenylethyl ]-N$^1$-[1(S)-(cyclohexylmethyl)-2(R),3(S)-dihydroxy-5-methylhexyl ]-2(R)-(4-thiazolylmethyl) butanediamide (a) 4(S)-(1-Methylethyl)-3-[1-oxo-3-(4-thiazolyl)-propyl-2-oxazolidinone: Thioformamide (8.52 g, 0.14 mol) was added to a stirred solution of the bromoketone of example 2, section (c) (7.12 g, 23.3 mmol) in THF (120 mL). The mixture was stirred at room temperature for 5 h. Thereafter, the mixture was diluted with Et$_2$O, washed with 10% (w/v) aqueous NaHCO$_3$ and then H$_2$O, dried (MgSO$_4$) and concentrated to dryness under reduced pressure to give 4(S)-(1-methylethyl)-3-[1-oxo-3-(4-thiazoly)propyl]-2-oxazolidinone (3.8 g, 61%); $^1$H NMR(CDCl$_3$) δ 8.75 (s,1H), 7.05 (s,1H), 4.47-4.40 (m, 1H), 4.30-4.16 (m,2H), 3.46-3.36 (m,2H), 3.28-3.17 (m,2H), 2.45-2.28 (m, 1H), 0.90 (d, J=7.1 Hz,3H), 0.86 (d, J=6.9 Hz,3H).

(b) 3-[4-tert-Butoxy-1,4-dioxo-2(R)-(4-thiazolylmethyl) butyl]-4(S)-(1-methylethyl)-2oxazolidinone: The product of section (a) of this example (825 mg, 3.07 mmol) was stereoselectively alkylated with tert-butyl 2-bromoacetate according to the procedure described in example 2, section (f) to give a mixture of the desired 3-[4-tert-butoxy-1,4-dioxo-2(R)-(4-thiazolylmethyl)butyl ]-4(S)-(1-methylethyl) -2-oxazolidinone (Rf=0.25, eluent: EtOAc-hexane, 1:2) and its corresponding 2(S)-epimer (Rf=0.41, eluent: EtOAc-hexane, 1:2) in a 7:1 ratio, respectively. Flash chromatography (SiO$_2$, eluent: EtOAc-hexane, 1:2) yielded the pure desired compound as a white solid (882 mg, 75%), $^1$H NMR(CDCl$_3$) δ 8.75 (S,1H), 7.14 (s,1H), 4.62-4.5 (m, 1H), 4.50-4.40 (m, 1H), 4.29-4.20 (m,2H), 3.19 (dd, J=6.4 Hz,14.2 Hz,1H), 3.02 (dd, J=7.5 Hz,14.2 Hz,1H), 2.84 (dd, J=9.8 Hz,16.6 Hz,1H), 2.49 (dd, J=4.7 j Hz,16.6 Hz,1H), 1.41 (s,9H), 0.95 (d, J=6.8 Hz,3H), 0.92 (d, J=7.0 Hz,3H).

(c) 4-{[1(S)-(Cyclohexylmethyl)-2(R),3(S)-dihydroxy-5-methylhexyl]amino}-4-oxo-3-(R)-(4-thiazolylmethyl) butanoic acid tert-butyl ester: The latter 2-oxazolidinone derivative (4.02 g, 10.5 mmol) was reacted with lithium hydroxide-hydrogen peroxide according/to the procedure of example 2, section (g) to give the monoprotected dicarboxylic acid of formula 2, i.e. the 4-tert-butyl ester of 2(R)-(4-thiazolylmethyl)butanedioic acid. Subsequent coupling of the latter compound (2.83 g, 10.4 mmol) with 2(S)-amino-1-cyclohexyl-6-methyl-3(R), 4(S)-heptanediol hydrochloride (3.21 g, 11.5 mmol) according to the coupling procedure of example 2, section (g) gave the desired protected amido acid as a white solid (3.75 g, 72%); $^1$H NMR(CDCl$_3$) δ 8.70 (s, 1H), 7.10 (s,1H), 5.96 (d, J=8.3 Hz,1H), 4.40-4.25 (m,2H), 3.40-2.70 (m,6H), 2.40 (dd, J=4.4 Hz,16.8 Hz,1H), 1.95-1.10 (m,17H), 1.40 (s,9H), 0.90 (d, J=6.6 Hz,3H), 0.80 (d, J=6.4 Hz,3H).

(d) The title compound: Under a N$_2$ atmosphere, TFA (6 mL) was added to a cooled solution (0°) of the product of section (c) of this example (3.7 g, 7.45 mmol) in CH$_2$Cl$_2$ (30 mL). After the addition, the reaction mixture was stirred at room temperature for 5.5 h. Another portion of TFA (6 mL) was added to the reaction mixture at 0°. The mixture was stirred at room temperature for 3 h. Thereafter, the mixture was diluted with Et$_2$O and concentrated to dryness under reduced pressure to give the corresponding deprotected amido acid (4.70 g).

The latter compound was used for the following coupling step without further purification. The latter compound (1.50 g, 3.40 mmol) was dissolved in DMF (18 mL). BOP·PF$_6$ (1.80 g, 4.08 mmol), (S)-N,N-dimethyl-2-[(1-phenylethyl) amino]acetamide [0.98 g, 4.76 mmol, described in example 1, section (a)] and DIPEA (1.78 mL, 10.2 mmol) were added serially to the solution. The mixture was stirred at room temperature for 1 h. Thereafter, the mixture was diluted with EtOAc, washed with a saturated aqueous solution of NaHCO$_3$, H$_2$O and then brine, dried (MgSO$_4$) and concentrated under reduced pressure. The residue was purified by flash chromatography (SiO$_2$, eluent: (EtOH$_2$-EtOAc-hexane, 1:5:5) to give the title compound as a white solid (857 mg, 40%); $^1$H NMR (400 MHz, CDCl$_3$) (approximately a 1:1 mixture of rotamers) δ 8.79 and 8.76 (2s,1H), 7.37-7.18 (m,6H), 7.07 (broad d, J=8 Hz,1H), 6.05 and 5.12 (2q, J=7.01 Hz,7.0 Hz,1H), 4.40 and 4.20 (2m, 1H), 4.37, 3.24 and 3.85, 3.73 (4d, J=16.2 Hz,16.2 Hz,17.9 Hz,17.9 Hz, 2H), 3.50-3.10 (m,5H), 2.93, 2.92, 2.90 and 2.87 (4s,6H), 2.67 (dd, J=10.2 Hz,17 Hz,1H), 2.54 (dd, J=4.8 Hz,17 Hz,1H), 1.98-1.85 (m,2H), 1.85-1.50 (m, 1H), 1.58 and 1.36 (2d, J=6.9 Hz,7.1 Hz, 3H),1.45-1.10 (m, 8H), 0.93 (d, J=6.7 Hz,3H), 0.91 and 0.84 (2d, J=6.5 Hz, 6.6 Hz, 3H ); FAB mass spectrum, m/z: 629 (M+H)$^+$, 651 (M+Na)$^+$; $[\alpha]^{25}_D$ –55.3° (c 1.00, MeOH).

EXAMPLE 5

Preparation of N$^4$-(Cyclohexylmethyl)-N$^4$-(2-morpholino-2-oxoethyl)-N$^1$-[1(S)-(cyclohexylmethyl)-2(R),3(S)-dihydroxy-5-methylhexyl]-2(R)-(cyclopropylmethyl) butanediamide (a) 3-(3-Cyclopropyl-1-oxopropyl)-4(S)-(1-methylethyl)-2-oxazolidinone: A solution of mixed anhydride was prepared by adding, under N$_2$, pivaloyl chloride (14.8 mL, 120 mmol) over a period of 5 min to a cooled solution (0°) of 4-pentenoic acid (12.3 mL, 120 mmol) and N-methylmorpholine (15.4 mL, 140 mmol). The mixture was stirred at 0° for 30 min. Meanwhile, a second solution was prepared by adding dropwise under N$_2$ a 1.4M solution of butyllithium in hexane (71 mL, 100 mmol) to a stirred cooled solution (–78°) of (S)-4-(1-methylethyl)-2-oxazolidinone (12.9 g, 100 mmol) in dry THF (300 mL) over a period of 45 min. (Note: The agitation was done by an overhead stirrer.) After stirring for 15 min at –78°, the latter solution was added by cannulation to the stirred solution of the mixed anhydride at –78° over a period of 20 min. The mixture was stirred for an additional 30 min at the same temperature. A saturated aqueous solution of NH$_4$Cl (50 mL) was added and the mixture was allowed to warm to room temperature. The mixture was diluted with H$_2$O (300 mL). The organic layer was separated. The aqueous layer was extracted with EtOAc (3X). The combined organic phases were dried (Na$_2$SO$_4$) and evaporated to dryness under reduced pressure to give an oily residue [i.e. 4(S)-(1-methylethyl)-3-(1 -oxo-4-pentenyl)-2-oxazolidinone].

The latter oil was dissolved in 175 mL of a 0.4M Et$_2$O solution of diazomethane. The resulting solution was cooled to 0°. Palladium(II) acetate (112 mg, 0.5 mmol) was added to the cooled solution. The solution bubbled vigorously. After the bubbling subsided, additional palladium(II) acetate (112 mg, 0.5 mmol) and the Et$_2$O solution of diazomethane (175 mL) were added and the ensuing bubbling was allowed to subside. The latter addition was repeated two more times. (The total amount of diazomethane solution added was 700 mL.) The mixture was filtered through diatomaceous earth. The filtrate was concentrated under reduced pressure. The residual oil was purified by chromatography (SiO$_2$, eluent: EtOAc-hexane, 1:4) followed by distillation (100° at 0.05 mm Hg) to give the desired 3-(3-cyclopropyl-1-oxopropyl)-2-oxazolidinone derivative (20.0 g, 89%); $^1$H NMR (CDCl$_3$) δ 4.41 (complex m, 1H), 4.28 (d, J=9.1 Hz,1H), 4.20 (dd, J=3.4 Hz,8.8 Hz,1H), 3.05 (m,2H), 2.36 (m, 1H), 1.55 (q, J=7.3 Hz,2H), 0.91 (d, J=7.2 Hz,3H), 0.87 (d, J=7.1 Hz,3H), 0.89 (m, 1H), 0.43 (m,2H), 0.08 (m,2H).

(b) 3-[4-tert-Butoxy-1,4-dioxo-2(R)-(cyclopropylmethyl) butyl ]-4(S)-(1-methylethyl)-2-oxazolidinone: A 1.4M solution of butyllithium in hexane (70.0 mL, 97.6 mmol) was added over a period of 20 min to a cooled solution (0°) of diisopropylamine (15.0 mL, 106 mmol) in dry THF (150 mL). After stirring at 0° for 15 min, the solution was cooled to −78°. A solution of the product of section (a) of this example (20.0 g, 88.8 mmol) in THF (40 mL) was added to the cooled solution over 45 min. The mixture was stirred for 1 h at −78°. 1,3-Dimethyl-3,4,5,6-tetrahydro-2(1H)-pyrimidinone (23.6 mL, 195 mmol) and then over a period of 10 min a solution of tert-butyl 2-bromoacetate (15.1 mL, 93.2 mmol) in THF (20 mL) were added serially to the mixture. After stirring for 1.5 h at −78°, the reaction mixture was quenched with a saturated aqueous solution of NH$_4$Cl and then allowed to warm to room temperature. The mixture was diluted with EtOAc (250 mL). The organic layer was separated, washed with 5% (w/v) aqueous citric acid (3X), a saturated aqueous solution of NaHCO$_3$ (2X) and brine, dried (Na$_2$SO$_4$) and concentrated to dryness under reduced pressure. The residual oil was crystallized from EtOAc/hexane to give the desired oxazolidine derivative as colorless crystals (21.7 g, 72%); mp 104°–105°; [α]$^{23}_D$ +52.8° (c 1.02, CHCl$_3$).

(c) The protected amide, 3(R)-(cyclopropylmethyl)-4-{[1(S)-(cyclohexylmethyl)-2-(R),3(S)-dihydroxy-5-methylhexyl]amino}-4-oxobutanoic acid tert-butyl Following the procedure of section (g) of example 2, the product of section (b) of this example (10.2 g, 30 mmol) was reacted with lithium hydroxide-hydrogen peroxide to give the desired monoprotected dicarboxylic acid, i.e. the 4-tert-butyl ester of 2(R)-(cyclopropylmethyl)butanedioic acid, as a colorless oil (6.65 g, 97%); [α]$^{23}_D$+16.1° (c 2.61 CHCl$_3$).

The latter compound (2.39 g, 10.5 mmol) was coupled with an equivalent amount 2(S)-amino-1-cyclohexyl-6-methyl-3(R),4(S)-heptanediol hydrochloride according the the coupling procedure of section (g) of example 2 to give the desired protected amido acid as a white crystalline material (3.74 g, 78%) after crystallization from EtOAc-hexane; mp 138°–139°; $^1$H NMR(CDCl$_3$) δ 5.87 (d, J=8.9 Hz,1H), 4.41 (broad s, 1H), 4.32 (dt, J=4.4 Hz,9.1 Hz,1H), 3.22 (broad s,2H), 2.68-2.39 (m,2H), 2.00-1.10 (complex m, 22H), 1.44 (s, 9H), 0.93 (d, J=6.7 Hz,2H), 0.83 (d, J=6.5 Hz,3H), 0.75-0.65 (m, 1H), 0.48 (m,2H), 0.08 (broad m, 1H).

(d) The title compound: The product of section (c) of this example (329 mg, 0.72 mmol) was deprotected with TFA (1.2 mL) in anhydrous CH$_2$Cl$_2$ (2.4 mL) at 0° for 10 min and then at room temperature for 1.5 h to give (after evaporation of the volatiles under reduced pressure) a crude product (369 mg). The crude product was triturated several times with Et$_2$O to give 3(R)-(cyclopropylmethyl)-4-{[1(S)-(cyclohexylmethyl)-2(R),3(S)-dihydroxy-5-methylhexyl]-amino}-4-oxobutanoic acid as a white solid (193 mg, 67%).

The latter compound (125 mg, 0.31 mmol), 4-{2-[(cyclohexylmethyl)amino ]-1-oxoethyl]morpholine (94.5 mg, 0.39 mmol, described in example 1) and DIPEA (69.1 mg, 0.53 mmol) were dissolved in DMF (1.6 mL). BOP-PF$_6$ (153 mg, 0.35 mmol) was added to the solution. The reaction mixture was stirred at room temperature for 100 min. Thereafter, the reaction mixture was diluted with EtOAc, washed successively with 1 N aqueous HCl, H$_2$O, a saturated aqueous solution of NaHCO$_3$ and brine, dried (MgSO$_4$) and concentrated to dryness under reduced pressure. The residue was purified by flash chromatography (SiO2, eluent: EtOAc) to give the title compound as a white solid (175 mg, 90%); $^1$H NMR(CDCl$_3$) δ (>4:1 mixture of rotamers) major rotamer: 6.42 (broad d, J=8.2 Hz,1H), 4.32 (d, J=15.8 Hz,1H), 4.25-4.11 (m, 1H), 3.85 (d, J=15.8 Hz,1H), 3.77-3.65 (m,4H), 3.65-3.54 (m,2H), 3.50-3.39 (m,2H), 3.32-3.11 (m,4H), 2.97-2.81 (m, 1H), 2.74-2.64 (m,2H),1.99-0.97 (m,29H), 0.92 (d, J=6.6 Hz,3H), 0.83 (d, J=6.5 Hz,3H), 0.77-0.62 (m, 1H), 0.53-0.41 (m,2H), 0.16-0.04 (m,2H); FAB mass spectrum, m/z: 620 (M+H)$^+$, 642 (M+Na)$^+$; [α]$^{25}_D$−22.8° (c 1.00, MeOH).

By applying the appropriate intermediates, the serial coupling and deprotection procedure illustrated by examples 2, 3, 4 and 5 can be used to prepare other compounds of formula 1, such a those exemplified in the table of the following example.

EXAMPLE 6

Plasma Renin Assay

The ability of the compounds of formula 1 to inhibit human renin can be demonstrated in the plasma renin assay. The assay is performed as follows: The test compound (i.e. the inhibitor) is dissolved in dimethylsulfoxide (1 mM stock solution) and diluted with an aqueous buffer solution of 270 mM 2-(N-morpholino)ethanesulfonic acid and 1% human serum albumin (pH 5.85, also containing dimercaprol and 8-hydroxyquinoline sulfate in accordance with the instructions of the RIA kit noted below) to give an assay mixture in which the final dimethylsulfoxide content is 1% (v/v).

A human plasma pool is used as the source of both the substrate (angiotensinogen) and the enzyme (renin). The reaction is initiated by the addition of 50 μL of human plasma pool to 50 μL of various concentrations of inhibitor in the 1% dimethylsulfoxide assay buffer. The plasma renin activity is measured by the amount of angiotensin I generated at pH 6.0 following a 2 h incubation at 37°.

Quantitation of angiotensin I is performed by radioimmunoassay (RIA kit from New England Nuclear-Dupont, Mississauga, ON, Canada). The enzymatic activity of renin is expressed in ng of angiotensin I generated (/mL/2 h). The extent of inhibition of the reaction is determined from the amount of angiotensin I generated in reference to a control prepared without inhibitor. Nonlinear regression analysis is used to calculate the IC$_{50}$ values, i.e. the molar concentration of the test compound required to cause a 50% inhibition of the enzyme activity.

The compounds of formula 1 exhibited IC$_{50}$'s in the range of 10$^{-6}$ to 10$^{-9}$ molar in this assay. The following table exemplifies results obtained for compounds of formula 1.

TABLE

| Compound of Formula 1 | FAB/MS (M + H)$^+$ | IC$_{50}$ (nM) |
|---|---|---|
| 1. N$^4$-benzyl-N$^4$-(2-morpholino-2-oxoethyl)-N$^1$-[1(S)-(cyclohexylmethyl)-2(R),3(S)-dihydroxy-5-methylhexyl]-2(R)-(cyclopropylmethyl) butanedi- | 614 | 94 |

TABLE-continued

| Compound of Formula 1 | FAB/MS (M + H)+ | IC$_{50}$ (nM) |
|---|---|---|
| amide | | |
| 2. N$^4$-benzyl-N$^4$-[2-(dimethylamino)-2-oxoethyl]-N$^1$-[1(S)-(cyclohexylmethyl)-2(R),3(S)-dihydroxy-5-methylhexyl]-2(R)-(cyclopropylmethyl)butanediamide | 572 | 56 |
| 3. N$^4$-[2-(dimethylamino)-2-oxoethyl]-N$^4$-2-phenylethyl]-N$^1$-[1(S)-(cyclohexylmethyl)-2(R),3(S)-dihydroxy-5-methylhexyl]-2(R)-(cyclopropylmethyl)butanediamide | 586 | 59 |
| 4. N$^4$-[2-(dimethylamino)-2-oxoethyl]-N$^4$-(3-phenylpropyl)-N$^1$-[1(S)-(cyclohexylmethyl)-2(R),3(S)-dihydroxy-5-methylhexyl]-2(R)-(cyclopropylmethyl)butanediamide | 600 | 220 |
| 5. N$^4$-benzyl-N$^4$-{2-[methyl(1,1-dimethylethyl)amino]-2-oxoethyl}-N$^1$-[1(S)-(cyclohexylmethyl)-2(R),3(S)-dihydroxy-5-methylhexyl]-2(R)-(cyclopropylmethyl)butanediamide | 614 | 290 |
| 6. N$^4$-benzyl-N$^4$-[2-(methylamino)-2-oxoethyl]-N$^1$-[1(S)-(cyclohexylmethyl)-2(R),3(S)-dihydroxy-5-methylhexyl]-2(R)-(cyclopropylmethyl)butanediamide | 558 | 350 |
| 7. N$^4$-(2-amino-2-oxoethyl)-N$^4$-benzyl-N$^1$-[1(S)-(cyclohexylmethyl)-2(R),3(S)-dihydroxy-5-methylhexyl]-2(R)-(cyclopropylmethyl)-butanediamide | 544 | 395 |
| 8. N$^4$-benzyl-N$^4$-{2-[(methoxy)methylamino]-2-oxoethyl}-N$^1$-[1(S)-(cyclohexylmethyl)-2(R),3(S)-dihydroxy-5-methylhexyl]-2(R)-(cyclopropylmethyl)butanediamide | 588 | 66 |
| 9. N$^4$-[2-(dimethylamino)-2-oxoethyl]-N$^4$-(1-naphthylmethyl)-N$^1$-[1(S)-(cyclohexylmethyl)-2(R),3(S)-dihydroxy-5-methylhexyl]-2(R)-(cyclopropylmethyl)butanediamide | 622 | 66 |
| 10. N$^4$-[2-(dimethylamino)-2-oxoethyl]-N$^4$-[(4-methoxyphenyl)methyl]-N$^1$-[1(S)-(cyclohexylmethyl)-2(R),3(S)-dihydroxy-5-methylhexyl]-2(R)-(cyclopropylmethyl)butanediamide | 602 | 440 |
| 11. N$^4$-benzyl-N$^4$-[2-(diethylamino)-2-oxoethyl]-N$^1$-[1(S)-(cyclohexylmethyl)-2(R),3(S)-dihydroxy-5-methylhexyl]-2(R)-(cyclopropylmethyl)butanediamide | 600 | 140 |
| 12. N$^4$-benzyl-N$^4$-{2-[methyl[2-(2-pyridinyl)ethyl]amino]-2-oxoethyl}-N$^1$-[1(S)-(cyclohexylmethyl)-2(R),3(S)-dihydroxy-5-methylhexyl]-2(R)-(cyclopropylmethyl)butanediamide | 663 | 34 |
| 13. N$^4$-[2-(dimethylamino)-2-oxoethyl]-N$^4$-(2-pyridinylmethyl)-N$^1$-[1(S)-(cyclohexylmethyl)-2(R),3(S)-dihydroxy-5-methylhexyl]-2(R)-(cyclopropylmethyl)butanediamide | 573 | 120 |
| 14. N$^4$-[2-(dimethylamino)-2-oxoethyl]-N$^4$-(3-pyridinylmethyl)-N$^1$-[1(S)-(cyclohexylmethyl)-2(R),3(S)-dihydroxy-5-methylhexyl]-2(R)-(cyclopropylmethyl)butanediamide | 573 | 350 |
| 15. N$^4$-{2-{methyl{2-[methyl(morpholinocarbonyl)amino]ethyl}amino}-2-oxoethyl}-N$^4$-[1(S)-phenylethyl]-N$^1$-[1(S)-(cyclohexylmethyl)-2(R),3(S)-dihydroxy-5-methylhexyl]-2(R)-[(2-amino-4-thiazolyl)methyl]butanediamide | 800 | 0.5 |
| 16. N$^4$-[2-(dimethylamino)-2-oxoethyl]-N$^4$-[1(R)-phenylethyl]-N$^1$-[1(S)-(cyclohexylmethyl)-2(R),3(S)-dihydroxy-5-methylhexyl]-2(R)-(cyclopropylmethyl)butanediamide | 586 | 460 |
| 17. N$^4$-[2-(dimethylamino)-2-oxoethyl]-N$^4$-[1(S)-phenylethyl]-N$^1$-[1(S)-(cyclohexylmethyl)-2(R),3(S)-dihydroxy-5-methylhexyl]-2(R)-(cyclopropylmethyl)butanediamide | 586 | 34 |
| 18. N$^4$-[2-(dimethylamino)-2-oxoethyl]-N$^4$-[1(S)-(1-naphthylethyl)]-N$^1$-[1(S)-(cyclohexylmethyl)-2(R),3(S)-dihydroxy-5-methylhexyl]-2(R)-(cyclopropylmethyl)butanediamide | 636 | 170 |
| 19. N$^4$-[2-(dimethylamino)-2-oxoethyl]-N$^4$-[2(R)-phenylpropyl]-N$^1$-[1(S)-(cyclohexylmethyl)-2(R),3(S)-dihydroxy-5-methylhexyl2]-2(R)-(cyclopropylmethyl)butanediamide | 600 | 69 |
| 20. N$^4$-[2-(dimethylamino)-2-oxoethyl]-N$^4$-[2(S)-phenylpropyl]-N$^1$-[1(S)-(cyclohexylmethyl)-2(R),3(S)-dihydroxy-5-methylhexyl]-2(R)-(cyclopropylmethyl)butanediamide | 600 | 37 |
| 21. N$^4$-[2-(dimethylamino)-2-oxoethyl]-N$^4$-(2-methyl-2-phenylpropyl)-N$^1$-[1(S)-(cyclohexylmethyl)-2(R),3(S)-dihydroxy-5-methylhexyl]-2(R)-(cyclopropylmethyl)butanediamide | 614 | 150 |
| 22. N$^4$-[1(S)-phenylethyl]-N$^4$-{2-{methyl[2-(2-pyridinyl)ethyl]-amino}-2-oxoethyl}-N$^1$-[1(S)-(cyclohexylmethyl)-2(R),3(S)-dihydroxy-5-methylhexyl]-2(R)-(cyclopropylmethyl)-butanediamide | 677 | 20 |
| 23. N$^4$-{2-{[2-(dimethylamino)ethyl]methylamino}-2-oxoethyl}-N$^4$-[1(S)-phenylethyl]-N$^1$-[1(S)-(cyclohexylmethyl)-2(R),3(S)-dihydroxy-5-methylhexyl]-2(R)-(cyplopropylmethyl)-butanediamide | 643 | 26 |
| 24. N$^4$-{2-{[2-(diethylamino)ethyl]methylamino}-2-oxoethyl}-N$^4$-[1(S)-phenylethyl]-N$^1$-[1(S)-(cyclohexylmethyl)-2(R),3(S)-dihydroxy-5-methylhexyl]-2(R)-(cyclopropylmethyl)-butanediamide | 671 | 61 |
| 25. N$^4$-[2-(dimethylamino)-2-oxoethyl]-N$^4$-[1(S)-phenylethyl]-N$^1$-[1(S)-(cyclohexylmethyl)-2(R),3(S)-dihydroxy-5-methylhexyl]-2(R)-propylbutanediamide | 574 | 34 |
| 26. N$^4$-benzyl-N$^4$-{2-{methyl[2-(2-pyridinyl)ethyl]amino}-2-oxoethyl}-N$^1$-[1(S)-(cyclohexylmethyl)-2(R),3(S)-dihydroxy-5-methylhexyl]-2(R)-propylbutanediamide | 651 | 29 |
| 27. N$^4$-[2-(dimethylamino)-2-oxoethyl]-N$^4$-[1(S)-phenylethyl]-N$^1$-[1(S)-(cyclohexylmethyl)-2(R),3(S)-dihydroxy-5-methylhexyl]-2(R)-(1H-imidazol-4-yl)methyl)butanediamide | 612 | 6 |
| 28. N$^4$-[2-(dimethylamino)-2-oxoethyl]-N$^4$-[1(S)-phenylethyl]-N$^1$-[1(S)-(cyclohexylmethyl)-2(R),3(S)-dihydroxy-5-methylhexyl -2(R)-[(2-amino-4-thiazolyl)methyl]butanediamide | 644 | 1.3 |
| 29. N$^4$-benzyl-N$^4$-{2-{methyl[2-(4-pyridinyl)ethyl]amino}-2-oxoethyl}-N$^1$-[1(S)-(cyclohexylmethyl)-2(R),3(S)-dihydroxy-5-methylhexyl]-2(R)-(cyclopropylmethyl)butanediamide | 663 | 68 |
| 30. N$^4$-[2-(dimethylamino)-2-oxoethyl]-N$^4$-[1(S)-phenylethyl]-N$^1$-[1(S)-(cyclohexylmethyl)-2(R),3(S)-dihydroxy-5-methylhexyl]-2(R)-(4-thiazolylmethyl)butanediamide | 629 | 2.5 |
| 31. N$^4$-(cyclohexylmethyl)-N$^4$-[2- | 578 | 13 |

TABLE-continued

| Compound of Formula 1 | FAB/MS (M + H)+ | IC$_{50}$ (nM) |
|---|---|---|
| (dimethylamino)-2-oxoethyl]-N$^1$-[1(S)-(cyclohexylmethyl)-2(R),3(S)-dihydroxy-5-methylhexyl]-2(R)-(cyclopropylmethyl)butanediamide | | |
| 32. N$^4$-[2-(dimethylamino)-2-oxoethyl]-N$^4$-[1(S)-phenylethyl]-N$^1$-[1(S)-(cyclohexylmethyl)-2(R),3(S)-dihydroxy-5-methylhexyl]-2(S)-(2-thienylmethyl)butanediamide | 628 | 13 |
| 33. N$^4$-[1(S)-phenylethyl]-N$^4$-(2-morpholino-2-oxoethyl)-N$^1$-[1(S)-(cyclohexylmethyl)-2(R),3(S)-dihydroxy-5-methylhexyl]-2(R)-(cyclopropylmethyl)butanediamide | 628 | 120 |
| 34. N$^4$-benzyl-N$^4$-{2-{methyl[2-(2-pyridinyl)ethyl]amino}-2-oxoethyl}-N$^1$-[1(S)-(cyclohexylmethyl)-2(R),3(S) dihydroxy-5-methylhexyl]-2(S)-(2-thienylmethyl)butanediamide | 705 | 13 |
| 35. N$^4$-(cyclohexylmethyl)-N$^4$-(2-morpholino-2-oxoethyl)-N$^1$-[1(S)-(cyclohexylmethyl)-2(R),3(S)-dihydroxy-5-methylhexyl]-2(R)-(cyclopropylmethyl)butanediamide | 620 | 8 |
| 36. N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(4-thiazolylmethyl)butanediamide | 621 | 1.5 |
| 37. N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(S)-(2-thiazolylmethyl)butanediamide | 621 | 1.6 |
| 38. N$^4$-[1(S)-cyclohexylethyl]-N$^4$-[2-(dimethylamino)-2-oxoethyl]-N$^1$-[1(S)-(cyclohexylmethyl)-2(R),3(S)-dihydroxy-5-methylhexyl]-2(R)-(cyclopropylmethyl)butanediamide | 592 | 8.3 |
| 39. N$^4$-(cyclohexylmethyl)-N$^4$-(2-morpholino-2-oxoethyl)-N$^1$-[1(S)-(cyclohexylmethyl)-2(R),3(S)-dihydroxy-5-methylhexyl]-2(S)-(2-thiazolylmethyl)butanediamide | 663 | 1.6 |
| 40. N$^4$-[2-(dimethylamino)-2-oxoethyl]-N$^4$-[2(S)-phenylpropyl]-N$^1$-[1(S)-(cyclohexylmethyl)-2(R),3(S)-dihydroxy-5-methylhexyl]-2(S)-(2-thiazolylmethyl)butanediamide | 643 | 6.7 |
| 41. N$^4$-benzyl-N$^4$-{2-{methyl[2-(2-pyridinyl)ethyl]amino}-2-oxoethyl}-N$^1$-[1(S)-(cyclohexylmethyl)-2(R),3(S)-dihydroxy-5-methylhexyl]-2(S)-(2-thiazolylmethyl)butanediamide | 706 | 3.5 |
| 42. N$^4$-[2-(dimethylamino)-2-oxoethyl)N$^4$-[1(S)-phenylethyl]-N$^1$-[1(S)-(cyclohexylmethyl)-2(S)-hydroxy-2-(1,5,5-trimethyl-2-oxopyrrolidin-3(S)-yl)ethyl]-2(R)-(cyclopropylmethyl)butanediamide | 625 | 55 |
| 43. N$^4$-[2-(dimethylamino)-2-oxoethyl]-N$^4$-[1(S)-phenylethyl]-N$^1$-[1(S)-(cyclohexylmethyl)-2(R),3(S)-dihydroxy-(3-cyclopropylpropyl)]-2(R)-[(2-amino-4-thiazolyl)methyl]-butanediamide | 628 | 6.8 |
| 44. N$^4$-[2-(dimethylamino)-2-oxoethyl]-N$^4$-[1(S)-phenylethyl]-N$^1$-[1(S)-(cyclohexylmethyl)-2(S)-hydroxy-2-(1,5,5-trimethyl-2-oxopyrrolidin-3(S)-yl)ethyl]-2(R)-[(2-amino-4-thiazolyl)methyl]butanediamide | 683 | 2.4 |
| 45. N$^4$-[2-(dimethylamino)-2-oxoethyl]-N$^4$-[1(S)-phenylethyl]-N$^1$-[1(S)-(cyclohexylmethyl)-2(R)-hydroxy-3-(1-methylethoxy)-3-oxopropyl]-2(R)-[(2-amino-4-thiazolyl)methyl]butanediamide | 644 | 16 |
| 46. N$^4$-(cyclohexylmethyl)-N$^4$-{2-{methyl-[2-(2-pyridinyl)-ethyl]amino}-2-oxoethyl]-N$^1$-[1(S)-(cyclohexylmethyl)-2(R),3(S)-dihydroxy-5-methylhexyl]-2(R)-(cyclopropylmethyl)butanediamide | 669 | 12 |
| 47. N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-[(2-methyl-4-thiazolyl)methyl]butanediamide | 635 | 18.5 |
| 48. N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 636 | 0.9 |
| 49. N$^4$-(cyclohexylmethyl)-N$^4$-(2-morpholino-2-oxoethyl)-N$^1$-[1(S)-(cyclohexylmethyl)-2(R),3(S)-dihydroxy-5-methylhexyl]-2(R)-[(2-amino-4-thiazolyl)methyl]butanediamide | 678 | 1.5 |
| 50. N$^4$-(cyclohexylmethyl)-N$^4$-{2-{methyl-[2-(2-pyridinyl)ethyl]-amino}-2-oxoethyl}-N$^1$-[1(S)-(cyclohexylmethyl)-2(R),3(S)-dihydroxy-5-methyl-hexyl]-2(R)-[(2-amino-4-thiazolyl)methyl]butanediamide | 727 | 2.2 |
| 51. N$^4$-[2-(dimethylamino)-2-oxoethyl] N$^4$-[2-(2-pyridinyl)ethyl]-N$^1$-[1(S)-(cyclohexylmethyl)-2(R),3(S)-dihydroxy-5-methylhexyl]-2(R)-(cyclopropylmethyl)butanediamide | 587 | 145 |
| 52. N$^4$-benzyl-N$^4$-[2-(dimethylamino)-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 630 | 3 |
| 53. N$^4$-benzyl-N$^4$-{2-{methyl[2-(2-pyridinyl) ethyl]amino}-2-oxoethyl]-N$^1$-[1(S)-(cyclohexylmethyl)-2(R),3(S)-dihydroxy-5-methylhexyl]-2(R)-(4-thiazolylmethyl)butanediamide | 706 | 2.5 |
| 54. N$^4$-[2-(dimethylamino)-2-oxoethyl]-N$^4$-[1(S)-phenylethyl]-N$^1$-[1(S)-(cyclohexylmethyl)-2(R),3(S)-dihydroxy-5-methylhexyl]-2(S)-(2-thiazolylmethyl)butanediamide | 629 | 4 |
| 55. N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(phenylmethyl)butanediamide | 614 | 16 |
| 56. N$^4$-[{1(S),2(S),4(S)- and 1(R),2(S),4(R)-[bicyclo[2.2.1]hept-2-yl}methyl]-N$^4$-[2-(dimethylamino)-2-oxoethyl]-N$^1$- [1(S)-(cyclohexylmethyl)-2(R),3(S)-dihydroxy-5-methylhexyl]-2(R)-(4-thiazolyl-methyl)butanediamide | 633 | 2 |
| 57. N$^4$-benzyl-N$^4$-{2-{methyl[2-(2-pyridinyl) ethyl]amino}-2-oxoethyl}-N$^1$-[1(S)-(cyclohexylmethyl)-2(R),3(S)-dihydroxy-5-methylhexyl]-2(R)-[(2-amino-4-thiazolyl)methyl]-butanediamide | 721 | 1 |
| 58. N$^4$-(cyclohexylmethyl)-N$^4$-[2-(dimethylamino)-2-oxoethyl]-N$^1$-[1(S)-(cyclohexylmethyl)-2(R) dihydroxy-5-methylhexyl]-2(R)-(3-pyridinylmethyl)butanediamide | 615 | 10 |

TABLE-continued

| Compound of Formula 1 | FAB/MS (M + H)+ | IC$_{50}$ (nM) |
|---|---|---|
| 59. N$^4$-(cyclohexylmethyl)-N$^4$-(2-morpholino-2-oxoethyl)-N$^1$-[1(S)-(cyclohexylmethyl)-2(R),3(S)-dihydroxy-5-methylhexyl]-2(R)-(3-pyridinylmethyl)butanediamide | 658 | 10 |
| 60. N$^4$-[2-(dimethylamino)-2-oxoethyl]-N$^4$-(2-phenylethyl)-N$^1$-[1(S)-(cyclohexylmethyl)-2(R),3(S)-dihydroxy-5-methylhexyl)-2(R)-[(2-amino-4-thiazolyl)methyl]butanediamide | 644 | 5 |
| 61. N$^4$-[2-(dimethylamino)-2-oxoethyl]-N$^4$-[2(S)-phenylpropyl]-N$^1$-[1(S)-(cyclohexylmethyl)-2(R),3(S)-dihydroxy-5-methylhexyl]-2(R)-[(2-amino-4-thiazolyl)methyl]-butanediamide | 658 | 3.5 |
| 62. N$^4$-[2-[4-(methoxymethoxy)piperidin-yl]-2-oxoethyl}-N$^4$-(cyclohexyl-methyl)-N$^1$-[1(S)-(cyclohexylmethyl)-2(R),3(S)-dihydroxy-5-methylhexyl]-2(R)-[(2-amino-4-thiazolyl)methyl]butanediamide | 736 | 3 |
| 63. N$^4$-{1(S)-cyclohexylethyl)-N$^4$-{2-{methyl[2-(2-pyridinyl)ethyl]-amino}-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 741 | 1 |
| 64. N$^4$-[2-(dimethylamino)-2-oxoethyl]-N$^4$-(2-pyridinylmethyl)-N$^1$-[1(S)-(cyclohexylmethyl)-2(R),3(S)-dihydroxy-5-methylhexyl]-2(R)-[(2-amino-4-thiazolyl)methyl]-butanediamide | 631 | 10 |
| 65. N$^4$-(cyclohexylmethyl)-N$^4$-{2-{methyl[2-(2-pyridinyl)ethyl]amino}-2-oxoethyl]-N$^1$-{1(S)-(cyclohexylmethyl)-2(R)-hydroxy-3-[(1-methyl-1H-tetrazol-5-yl)thio]propyl]-2(R)-[(2-amino-4-thiazolyl)methyl]-butanediamide | 769 | 45 |
| 66. N$^4$-(cyclohexylmethyl)-N$^4$-{2-{methyl[2-(2-pyridinyl)ethyl]amino}-2-oxoethyl]-N$^1$-[1(S)-(cyclohexylmethyl)-2(R),3(S)-dihydroxy-5-methyl-hexyl]-2(R)-(3-pyridinylmethyl)-butanediamide | 706 | 10 |
| 67. N$^4$-(cyclohexylmethyl)-N$^4$-(2-morpholino-2-oxoethyl)-N$^1$-[1(S)-(cyclohexylmethyl)-2(R),3(S)-dihydroxy-5-methylhexyl]-2(R)-(2-pyridinylmethyl)butanediamide | 657 | 4 |
| 68. N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(2-pyridinylmethyl)butanediamide | 615 | 4 |
| 69. N$^4$-(cyclopentylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(3-pyridinylmethyl)butanediamide | 601 | 32 |
| 70. N$^4$-(cycloheptylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(3-pyridinylmethyl)butanediamide | 630 | 7 |
| 71. N$^4$-(cyclopentylmethyl)-N$^4$-{2-{methyl [2-(2-pyridinyl) ethyl]-amino}-2-oxoethyl]-N$^1$-[1(S)-(cyclohexylmethyl)-2(R),3(S)-dihydroxy-5-methylhexyl]-2(R)-[[(2-amino-4-thiazolyl)methyl]butanediamide | 713 | 1 |
| 72. N$^4$-{methyl]2-(2-pyridinyl)ethyl}-amino}-2-oxoethyl]-N$^4$-(2-thienyl-methyl)-N$^1$-[1(S)-(cyclohexylmethyl)-2(R),3(S)-dihydroxy-5-methylhexyl]-2(R)-[(2-amino-4-thiazolyl)methyl]-butanediamide | 727 | 2 |
| 73. N$^4$-[2-(dimethylamino)-2-oxoethyl]-N$^4$-[(3,5-dimethylphenyl)methyl]-N$^1$-[1(S)-(cyclohexylmethyl)-2(R),3(S)-dihydroxy-5-methylhexyl]-2(R)-[(2-amino-4-thiazolyl)methyl]butanediamide | 658 | 3 |
| 74. N$^4$-(cyclohexylmethyl)-N$^4$-{2-{methyl-[2-(2-pyridinyl)ethyl]amino}-2-oxoethyl]-N$^1$-[1(S)-(cyclohexylmethyl)-2(R)-hydroxy-3-(1-methylethoxy)-3-oxopropyl]-2(R)-[(2-amino-4-thiazolyl)methyl]butanediamide | 727 | 18 |
| 75. N$^4$-[2-{methyl[2-(2-pyridinyl)ethyl]-amino}-2-oxoethyl]-N$^4$-[1(S)-phenylethyl]-N$^1$-[1(S)-(cyclohexylmethyl)-2(R),3(S)-dihydroxy-5-methylhexyl]-2(R)-[(2-amino-4-thiazolyl)methyl]butanediamide | 735 | 1 |
| 76. N$^4$-(cyclohexylmethyl)-N$^4$-{2-{methyl [2-(3-pyridinyl)ethyl]-amino}-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 727 | 0.4 |
| 77. N$^4$-(cyclohexylmethyl)-N$^4$-{2-{methyl[2-(2-pyridinyl)ethyl]-amino}-2-oxoethyl]-N$^1$-[1(S)-(cyclohexylmethyl)-2(S)-hydroxy-5-methylhexyl]-2(R)-[(2-amino-4-thiazolyl)methyl]butanediamide | 711 | 36 |
| 78. N$^4$-(cycloheptylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 650 | 0.6 |
| 79. N$^4$-(2-furanylmethyl)-N$^4$-{2-{methyl-[2-(2-pyridinyl)ethyl]amino}-2-oxoethyl]-N$^1$-[1(S)-(cyclohexylmethyl)-2(R),3(S)-dihydroxy-5-methyl-hexyl]-2(R)-[(2-amino-4-thiazolyl)-methyl]butanediamide | 711 | 1 |
| 80. N$^4$-(cyclopentylmethyl)-N$^4$-(2-morpholino-2-oxoethyl)-N$^1$-[1(S)-(cyclohexylmethyl)-2(R),3(S)-dihydroxy-5-methylhexyl]-2(R)-[(2-amino-4-thiazolyl)methyl]butanediamide | 664 | 2 |
| 81. N$^4$-(cycloheptylmethyl)-N$^4$-{2-{methyl[2-(2-pyridinyl)ethyl]amino}-2-oxoethyl]-N$^1$-[1(S)-(cyclohexylmethyl)-2(R),3(S)-dihydroxy-5-methyl-hexyl]-2(R)-[(2-amino-4-thiazolyl)-methyl]butanediamide | 742 | 1 |
| 82. N$^4$-[(2-fluorophenyl)methyl]-N$^4$-{2-{methyl[2-(2-pyridinyl)ethyl]-amino}-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 739 | 3 |
| 83. N$^4$-(cyclohexylmethyl)-N$^4$-{2-{methyl{2-[methyl(morpholinocarbonyl)-amino]ethyl}amino}-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 792 | 0.35 |
| 84. N$^4$-(2-ethylbutyl)-N$^4$-{2-{methyl[2-(2-pyridinyl)ethyl]amino}-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 715 | 3 |

TABLE-continued

| Compound of Formula 1 | FAB/MS (M + H)+ | IC$_{50}$ (nM) |
|---|---|---|
| 85. N$^4$-(cyclopentylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide | 622 | 1 |
| 86. N$^4$-{2-{methyl[2-(2-pyridinyl)ethyl]amino}-2-oxoethyl}-N$^4$-(2-thiazolylmethyl)-N$^1$-[1(S)-(cyclohexylmethyl)-2(R),3(S)-dihydroxy-5-methylhexyl]-2(R)-[(2-amino-4-thiazolyl)methyl]butanediamide | 728 | 6 |
| 87. N$^4$-(2-cyclopentylethyl)-N$^4$-{2-{methyl[2-(2-pyridinyl)ethyl]amino}-2-oxoethyl}-N$^1$-[1(S)-(cyclohexylmethyl)-2(R),3(S)-dihydroxy-5-methylhexyl]-2(R)-[(2-amino-4-thiazolyl)methyl]butanediamide | 727 | 2 |
| 88. N$^4$-{2-{methyl[2-(2-pyridinyl)ethyl]amino}-2-oxoethyl}-N$^4$-[(3-methyl-2-thienyl)methyl]-N$^1$-[1(S)-(cyclohexylmethyl)-2(R),3(S)-dihydroxy-5-methylhexyl]-2(R)-[(2-amino-4-thiazolyl)methyl]butanediamide | 741 | 4 |
| 89. N$^4$-(3-furanylmethyl)-N$^4$-{2-{methyl[2-(2-pyridinyl)ethyl]amino}-2-oxoethyl}-N$^1$-[1(S)-(cyclohexylmethyl)-2(R),3(S)-dihydroxy-5-methylhexyl]-2(R)-[(2-amino-4-thiazolyl)methyl]butanediamide | 711 | 3 |
| 90. N$^4$-(cyclohexylmethyl)-N$^4$-{2-[methyl-(2-morpholinoethyl)amino]-2-oxoethyl}-N$^1$-[1(S)-(cyclohexylmethyl)-2(R),3(S)-dihydroxy-5-methylhexyl]-2(R)-[(2-amino-4-thiazolyl)methyl]butanediamide | 735 | 0.5 |
| 91. N$^4$-{2-{methyl[2-(2-pyridinyl)ethyl]amino}-2-oxoethyl}-N$^4$-(1-propylbutyl)-N$^1$-[1(S)-(cyclohexylmethyl)-2(R),3(S)-dihydroxy-5-methylhexyl]-2(R)-[(2-amino-4-thiazolyl)methyl]butanediamide | 729 | 8 |
| 92. N$^4$-{2-{methyl[2-(2-pyridinyl)ethyl]amino}-2-oxoethyl}-N$^4$-(2-propylpentyl)-N$^1$-[1(S)-(cyclohexylmethyl)-2(R),3(S)-dihydroxy-5-methylhexyl]-2(R)-[(2-amino-4-thiazolyl) methyl]butanediamide | 744 | 5 |
| 93. N$^4$-{2-[methyl(2-morpholinoethyl)amino]-2-oxoethyl}-N$^4$-[1(S)-phenylethyl]-N$^1$-[1(S)-(cyclohexylmethyl)-2(R),3(S)-dihydroxy-5-methylhexyl]-2(R)-[(2-amino-4-thiazolyl)methyl]butanediamide | 743 | 2 |

Other compounds of formula 1 include:

N$^4$-(2-ethyl-2-methylbutyl)-N$^4$-{2-{methyl [2-(2-pyridinyl)ethyl]amino}-2-oxoethyl}-N$^1$-[1(S)-(cyclohexylmethyl)-2(R),3(S)-dihydroxy-5-methylhexyl ]-2(R)-[(2-amino-4-thiazolyl)methyl]butanediamide, N$^4$-[2-(dimethylamino)-2-oxoethyl]-N$^4$-[1(S)-phenylethyl]-N$^1$-[1(S)-(cyclohexylmethyl)-2(S)-hydroxy-5-methylhexyl ]-2-(R)-(4-thiazolylmethyl)-butanediamide, N$^4$-[2-(dimethylamino)-2-oxoethyl]-N$^4$-[1(S)-phenylethyl]-N$^1$-[1(S)-(cyclohexylmethyl)-2(S)-hydroxy-5-methylhexyl]-2(S)-(2-thiazolylmethyl)-butanediamide, N$^4$-(cyclohexylmethyl)-N$^4$-[2-(dimethylamino)-2-oxoethyl]-N$^1$-[1-(S)-(cyclohexylmethyl)-2(S)-hydroxy-2-(1,5,5-trimethyl-2-oxopyrrolidin-3-(S)-yl)ethyl]-2(R)-[(2-amino-4-thiazolyl)methyl]butanediamide, N$^4$-(cyclohexylmethyl)-N$^4$-(2-morpholino-2-oxoethyl)-N$^1$-[1(S)-(cyclohexylmethyl)-2(S)-hydroxy-2-(1,5,5-trimethyl-2-oxopyrrolidin-3(S)-yl)ethyl]-2(R)-(4-thiazolylmethyl)butanediamide, N$^4$-(cyclohexylmethyl)-N$^4$-[2-(dimethylamino)-2-oxoethyl]-N$^1$-[1(S)-(cyclohexylmethyl)-2(S)-hydroxy-3-cyclopropylpropyl]-2(S)-(2-thiazolylmethyl)butanediamide, N$^4$-(cyclohexylmethyl)-N$^4$-{2-{methyl[2-(2-pyridinyl)ethyl]amino}-2-oxoethyl}-N$^1$-[1(S)-(cyclohexylmethyl-2(S)-hydroxy-3-cyclopropylpropyl ]-2(R)-[(2-amino-4-thiazolyl)methyl]butanediamide, N$^4$-[2-(dimethylamino)-2-oxoethyl]-N$^4$-[1(S)-phenylethyl]-N$^1$-[1(S)-(cyclohexylmethyl)-2(S)-hydroxy-4-methylpentyl]-2(R)-(4-thiazolylmethyl)butanediamide, N$^4$-(cyclohexylmethyl)-N$^4$-(2-morpholino-2-oxoethyl)-N$^1$-[1(S)-(cyclohexylmethyl)-2(S)-hydroxy-4-methylpentyl]-2(S)-(2-thiazolylmethyl)butanediamide, N$^4$-(cyclohexylmethyl)-N$^4$-(2-morpholino-2-oxoethyl)-N$^1$-[1(S)-(cyclohexylmethyl)-2-(R)-hydroxy-3-(1-methylethoxy)-3-oxopropyl]-2-(R)-(4-thiazolylmethyl)butanediamide, N$^4$-(cyclohexylmethyl)-N$^4$-{2-methyl[2-(2-pyridinyl)ethyl]amino}-2-oxoethyl}-N$^1$-[1(S)-(cyclohexylmethyl)-2(R)-hydroxy-3-(1-methylethoxy)-3-oxopropyl]-2(S)-(2-thiazolylmethyl)butanediamide, N$^4$benzyl-N$^4$-{2-[4-(methoxymethoxy)-1-piperidinyl]-2-oxoethyl}-N$^1$-[1(S)-(cyclohexylmethyl)-2(R),3(S)-dihydroxy-5-methylhexyl]-2(R)-[(2-amino-4-thiazolyl)methyl]butanediamide, N$^4$-{2-{methyl[2-(3-pyridinyl)ethyl]amino}-2-oxoethyl}-N$^4$-[1(S)-phenylethyl]-N$^1$-[1(S)-(cyclohexylmethyl)-2(R),3(S)-dihydroxy-5-methylhexyl ]-2(R)-[(2-amino-4-thiazoly)methyl]butanediamide, N$^4$-{2-[methyl(2-pyridinylmethyl)amino]-2-oxoethyl}-N$^4$-[1(S)-phenylethyl ]-N$^1$-[1(S)-(cyclohexylmethyl)-2(R),3(S)-dihydroxy-5-methylhexyl]-2(R)-[(2-amino-4-thiazolyl)methyl]butanediamide, N$^4$-{2-{methyl[3-(2-pyridinyl)propyl]amino}-2-oxoethyl}-N$^4$-[1(S)-phenylethyl ]-N$^1$-[1(S)-(cyclohexylmethyl)-2(R),3(S)-dihydroxy-5-methylhexyl]-2(R)-[(2-amino-4-thiazolyl)methyl]butanediamide, N$^4$-{2-{methyl[2-(2-pyridinyl)ethyl]amino}-2-oxoethyl}-N$^4$-(2-pyridinylmethyl)-N$^1$-[1(S)-(cyclohexylmethyl)-2(R),3(S)-dihydroxy-5-methylhexyl]-2(R)-[(2-amino-4-thiazolyl)methyl]butanediamide, N$^4$-{2-{methyl[2-(2-pyridinyl)ethyl]amino}-2-oxoethyl}-N$^4$-(3-pyridinylmethyl)-N$^1$-[1(S)-(cyclohexylmethyl)-2(R),3(S)-dihydroxy-5-methylhexyl ]-2(R)-[(2-amino-4-thiazolyl)methyl]butanediamide, N$^4$-[(1-methylcyclohexyl)methyl]-N$^4$-{2-{methyl[2-(2-pyridinyl)ethyl ]amino}-2-oxoethyl}-N$^1$-[1(S)-(cyclohexylmethyl)-2(R),3(S)-dihydroxy-5-methylhexyl]-2(R)-[(2-amino-4-thiazolyl)methyl]butanediamide, N$^4$-[2-(4-hydroxy-1-piperidinyl)-2-oxoethyl]-N$^4$-(cyclohexylmethyl)-N$^1$-[1(S)-(cyclohexylmethyl)-2(R)-,3(S)-dihydroxy-5-methylhexyl]-2(R)-[(2-amino-4-thiazolyl)methyl]butanediamide, N$^4$-{2-[methyl(3-morpholino-3-oxopropyl)amino]-2-oxoethyl]-N$^4$-[1(S)-phenylethyl ]-N$^1$-[1(S)-(cyclohexylmethyl)-2(R),3(S)-dihydroxy-5-methylhexyl]-2(R)-[(2-amino-4-thiazolyl)methyl]butanediamide, N$^4$-{2-{methyl[2-(4-methyl-1-piperazinyl)ethyl]amino}-2-oxoethyl}-N$^4$-[1(S)-phenylethyl]-N$^1$-[1(S)-(cyclohexylmethyl)-2(R),3(S)-dihydroxy-5-methylhexyl]-2(R)-[(2-amino-4-thiazolyl)methyl]butanediamide.

We claim:

1. A method for treating renin-dependent congestive heart failure in a mammal suffering from renin-dependent congestive heart failure which comprises administering to said mammal a renin-inhibiting amount of a compound of formula 1

$$A-N(R^1)C(O)CH_2CH(R^2)C(O)-B \quad (1)$$

wherein A is $R^3R^4NC(O)CH_2$ wherein (a) $R^3$ is hydrogen or lower alkyl and $R^4$ is hydrogen, lower alkyl or lower alkyl monosubstituted with lower cycloalkyl or phenyl; or (b) $R^3$ hydrogen or lower alkyl and $R^4$ is lower alkyl monosubstituted with a heterocyclic ring (hereinafter designated as "Het") which is an unsubstituted, mono-substituted or disubstituted, five- or six-membered ring containing one or two heteroatoms selected from the group consisting of N, O and S, and wherein each substituent is selected independently from the group consisting of lower alkyl, lower alkoxy, halo, amino or lower alkylamino; or (c) $R^3$ is lower alkyl and $R^4$ is $R^5R^6N$-Alk wherein $R^5$ and $R^6$ each is hydrogen or lower alkyl and Alk is a divalent alkyl radical derived by the removal of two hydrogen atoms of a straight or branched chain hydrocarbon containing from one to six carbon atoms; or (d) $R^3$ is lower alkyl and $R^4$ is $R^{5A}R^{6A}NCH_2CH_2$ wherein $R^{5A}$ is lower alkyl and $R^{6A}$ is piperidinocarbonyl, morpholinocarbonyl, thiomorpholinocarbonyl, piperazinocarbonyl or 4-(lower alkyl)-1-piperazinylcarbonyl; or (e) $R^3$ is lower alkyl and $R^4$ is $QC(O)(CH_2)_m$ wherein Q is piperidino, morpholino, thiomorpholino, piperazino or 4-(lower alkyl)-1-piperazinyl and m is the integer 1 or 2; or (f) $R^3$ is lower alkyl and $R^4$ is lower alkoxy; or (g) $R^3$ and $R^4$ together with the nitrogen atom to which they are attached form a pyrrolidino, piperidino, 4-hydroxy-1-piperidinyl, 4-[(lower alkoxy)-(lower alkoxy)]-1-piperidinyl, morpholino, thiomorpholino, piperazino or 4-(lower alkyl)-1-piperazinyl;

$R^1$ is (1–8C)alkyl or lower alkyl monosubstituted with lower cycloalkyl, 1-(lower alkyl)-(lower cycloalkyl), bicyclo[2.2.1]hept-2-yl, phenyl, 2-(lower alkyl)phenyl, 2-(lower alkoxy)phenyl, 2-halophenyl, 4-(lower alkyl)phenyl, 4-(lower alkoxy)phenyl, 4-halophenyl, 3,5-di (lower alkyl)phenyl, 3,4-methylenedioxyphenyl, 1-naphthyl, 2-naphthyl or Het wherein Het is a defined in this claim;

$R^2$ is lower alkyl, (lower cycloalkyl)methyl, benzyl or Het-$CH_2$ wherein Het is as defined in this claim; and B is $NHCH(R^7)CH(OH)$-Z wherein $R^7$ is lower alkyl, (lower cycloalkyl)methyl, benzyl, [4-(lower alkyl) phenyl]methyl, [4-(lower alkoxy)phenyl]methyl, or (4-halophenyl)methyl, and Z is lower alkyl, lower cycloalkyl, (lower cycloalkyl)methyl, $C(O)OR^8$ wherein $R^8$ is lower alkyl, the radical of formula 2

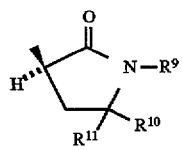

wherein $R^9$ is lower alkyl and $R^{10}$ and $R^{11}$ each is hydrogen or lower alkyl, methyl or $CH(O)R^{12}$ wherein $R^{12}$ is lower alkyl or lower cycloalkyl, with the provisos (1) that the asymmetric carbon atom bearing $R^7$ has the (S) configuration, (2) that when Z is lower alkyl, lower cycloalkyl, (lower cycloalkyl)methyl or the radical of formula 2 as defined in this claim then the asymmetric carbon atom bearing the hydroxyl in the $NHCH(R^7)CH(OH)$ radical has the (S) configuration, (3) that when Z is $C(O)OR^8$ wherein $R^8$ is lower alkyl, or when Z is[(1-methyl-1H-tetrazol-5-yl)thio]methyl, then the asymmetric carbon atom bearing the hydroxyl in the $NHCH(R^7)CHOH$ radical has the (R) configuration, and (4) that when Z is $CH(OH)R^{12}$ wherein $R^{12}$ is lower alkyl or lower cycloalkyl the asymmetric carbon atoms bearing the hydroxyls in the NHCH $(R^7)CH(OH)$ and Z radicals have respectively the (R) and (S) configuration; with the additional proviso that the carbon atom bearing $R^2$ has the (R) configuration, except when $R^2$ is $CH_2$-Het wherein Het has a nitrogen atom at the point of attachment, and/or Het to the methylene ($CH_2$), then in the instance of this exception the carbon atom bear $R^2$ has the (S) configuration; or a pharmaceutically acceptable acid addition salt thereof.

2. The method as recite in claim 1 comprising administering the compound of formula 1 wherein $$A \text{ is } R^3R^4NC(O)CH_2$$

wherein (a) $R^3$ is lower alkyl and $R^4$ is lower alkyl or lower alkyl monosubstituted with phenyl; or (b) $R^3$ is lower alkyl and $R^4$ is lower alkyl monosubstituted with Het wherein Het is as defined in claim 1;

(c) $R^3$ is lower alkyl and $R^4$ is $R^5R^6N$-Alk wherein $R^5$ and $R^6$ each is lower alkyl and Alk is as defined in claim 1;

(d) $R^3$ is lower alkyl and $R^4$ is $R^{5A}R^{6A}NCH_2CH_2$ wherein $R^{5A}$ is lower alkyl and $R^{6A}$ is piperidinocarbonyl, morpholinocarbonyl or 4-methyl-1-piperazinylcarbonyl; or (e) $R^3$ is lower alkyl and $R^4$ is 2-morpholino-2-oxoethyl, 3-morpholino-3-oxopropyl or 3-(4-methyl-1-piperazinyl)-3-oxopropyl; or (f) $R^3$ is lower alkyl and $R^4$ is lower alkoxy; or (g) $R^3$ and $R^4$ together with the nitrogen atom to which they are attached form a pyrrolidino, piperidino, 4-hydroxypiperidinyl, 4-(methoxymethoxy)-1-piperidinyl, morpholino, thiomorpholino or 4-methyl-1-piperazinyl;

$R^1$ is (1–8C)alkyl or lower alkyl monosubstituted with lower cycloalkyl, 1(lower alkyl)-(lower alkyl), bicyclo [2.2.1]hept-2-yl, phenyl, 2-methylphenyl, 2-fluorophenyl, 4-methylphenyl, 4-methoxyphenyl, 4-chlorophenyl, 4-fluorophenyl, 3,5-dimethylphenyl, (3,4-methylenedioxy)phenyl, 1-naphthyl, 2-naphthyl or Het wherein Het is as defined in claim 1;

$R^2$ is lower alkyl, (lower cycloalkyl)methyl, benzyl, 1H-imidazol-2-ylmethyl, 1H-imidazol-4-ylmethyl, (1-methyl-1H-imidazoyl-4-yl)methyl, 2-thienylmethyl, 2-oxazolylmethyl, 4-oxazolylmethyl, 2-thiazolylmethyl, 4-thiazolylmethyl, (2-methyl-4-thiazolyl)methyl, (2-amino-4-thiazolyl)methyl,[2-(methylamino)-4-thiazolyl]methyl, 2-pyridinylmethyl or 3-pyridinylmethyl; and B is as defined in claim 1; or a pharmaceutically acceptable acid addition salt thereof.

3. The method as recited in claim 2 comprising administering a compound of formula 1 wherein A is $R^3R^4NC(O)$ $CH_2$ wherein $R^3$ is methyl, ethyl or propyl and $R^4$ is methyl, ethyl, propyl, 1,1-dimethylethyl, 2-(dimethylamino)ethyl, 2-(diethylamino)ethyl, or Het-$(CH_2)_n$ wherein Het is 2pyrrolyl, 2-furanyl, 2-thienyl, 1H-imidazol-2-yl, 1H-imidazol-4-yl, 2-isoxazolyl, 2-thiazolyl, 4-thiazolyl, 2-amino-4-thiazolyl, morpholino, 4-methyl-1-piperazinyl, 2-pyridinyl, 3-pyridinyl, 4-pyridinyl or 2-pyrimidinyl and n is the integer 1, 2 or 3; or $R^3$ is methyl and $R^4$ is 2-[methyl (morpholinocarbonyl)amino]ethyl or 2-{methyl[(4-methyl-1-piperazinyl)carbonyl]amino}ethyl; or $R^3$ is methyl and $R^4$ is 3-morpholino-3-oxopropyl or 3-(4-methyl-1-piperazinyl)-3-oxopropyl; or $R^3$ is methyl and $R^4$ is methoxy; or $R^3$ and $R^4$ together with the nitrogen to which they are attached form a pyrrolidino, piperidino, 4-hydroxy-1-piperidinyl, 4-(methoxymethoxy)-1-piperidinyl, morpholino or 4-methyl-1-piperazinyl; $R^1$ is 2-methylpropyl, 2-ethylbutyl, 1-propylbutyl, 2-propylpentyl, cyclopentylmethyl, 2-cyclopentyl-ethyl, 2-cyclohexylmethyl, (S)-1-cyclohexylethyl, 2-cyclohexylethyl, cycloheptylmethyl, (1-methylcyclo-hexyl)methyl, (1-methylcycloheptyl) methyl, (bicyclo[2.2.1]hept-2-yl)methyl, benzyl, (S)-1-phenylethyl, 2-phenylethyl, (R or S)-2-phenyl-propyl, 2-methyl-2-phenylpropyl, 3-phenylpropyl, (2-fluorophenyl) methyl, (2-methylphenyl)methyl, (4-methoxyphenyl) methyl, (4-chlorophenyl)methyl, (4-fluorophenyl)methyl, (3,5-dimethylphenyl)methyl, 1-naphthylmethyl, (S)-[1-(1-naphthyl)ethyl], 2-naphthylmethyl, 2-pyrrolylmethyl, 1H-imidazol-2-yl-methyl, 1H-imidazol-4-ylmethyl, 2-pyridinylmethyl, 3-pyridinylmethyl, 2-furanylmethyl, 3-furanylmethyl, 2-thienylmethyl, (3-methyl-2-thienyl) methyl, 2-oxazolylmethyl, 4-oxazolylmethyl, 2-thiazolylmethyl or (2-amino-4-thiazoly)methyl; $R^2$ is propyl, 2-methylpropyl, cyclopropylmethyl, cyclopentylmethyl, cyclohexylmethyl, benzyl, 1H-imidazol-2-ylmethyl, 1H-imidazol-4-ylmethyl, (1-methyl-1H-imidazol-4-yl)methyl, 2-thienylmethyl, 2-oxazolylmethyl, 4-oxazolylmethyl, 2-thiazolylmethyl, 4-thiazolylmethyl, (2-methyl-4-thiazolyl)methyl, (2-amino-4-thiazolyl)methyl, [2-(methylamino)-4-thiazolyl]methyl, 2-pyridinylmethyl or 3-pyridinylmethyl; and B is [1-(S)-(2-methylpropyl)-2(S)-hydroxy-5-methylhexyl]amino, [1(S)-(cyclohexylmethyl)-2(S)-hydroxy-5-methylhexyl]amino, {1(S)-[(4-methoxylphenyl)methyl]-2(S)-hydroxy-5-methylhexyl}amino, [1(S)-(cyclohexylmethyl)-2(S)-hydroxy-4-methylpentyl]amino, [1(S)-(cyclohexylmethyl)-2(S)-hydroxy-(3-cyclopropylpropyl)]amino, [1(S)-(2-methylpropyl)-2(R),3(S)-dihydroxy-5-methylhexyl]amino, [1(S)-(cyclohexylmethyl)-2(R),3(S)-dihydroxy-5-methylhexyl]amino, {1(S)-[(4-methoxyphenyl)methyl]-2(R),3(S)-dihydroxy-5-methylhexyl}amino, [1(S)-(2-methylpropyl)-2(R),3(S)-dihydroxy-(3-cyclopropylpropyl)] amino, [1(S)-(cyclohexylmethyl)-2(R),3(S)-dihydroxy-(3-cyclopropylpropyl]amino, [1(S)-(phenylmethyl)2(R),3(S)-dihydroxy(3-cyclopropylpropyl)]amino, {1(S)-[(4-methoxyphenyl)methyl]-2(R),3(S)-dihydroxy-3-cyclopropylpropyl}amino, [1(S)-(cyclohexylmethyl)-2(R)-hydroxy-3-(1-methylethoxy)-3-oxopropyl]amino, [1(S)-(cyclohexylmethyl)-2(S)-hydroxy-2-(1,5,5-trimethyl-2-oxo-pyrrolidin-3(S)-yl)ethyl]amino or {1(S)-(cyclohexylmethyl)-2(R)-hydroxy-3-[(1-methyl-1H-tetrazol-5-yl)thio]propyl}amino; or a pharmaceutically acceptable acid addition salt thereof.

4. The method as recited in claim 3 comprising administering the compound of formula 1 wherein A is $R^3R^4NC(O)CH_2$ wherein $R^3$ is methyl and $R^4$ is methyl, 2-(dimethylamino)ethyl, 2-(diethylamino)ethyl, 2-(2-pyrrolyl)ethyl, 2-(2-furanyl)ethyl, 2-(1H-imidazol-2-yl) ethyl, 2-(1H-imidazol-4-yl)ethyl, 2-(2-thiazolyl)ethyl, 2-morpholinoethyl, 2-(2-pyridinyl)-ethyl, 2-(3-pyridinyl) ethyl, 2-(4-pyridinyl)ethyl or 2-(2-pyrimidinyl)ethyl; or $R^3$ is methyl and $R^4$ is 2-[methyl(morpholinocarbon)amino] ethyl; or $R^3$ is methyl and $R^4$ is methoxy; or $R^3$ and $R^4$ together with the nitrogen atom to which they are attached form a pyrrolidino, piperidino, 4-hydroxy-1-piperidinyl, 4-(methoxymethoxy)-1-piperidinyl, morpholino or 4-methyl-1-piperazinyl; $R^1$ is 2-ethylbutyl, 1-propylbutyl, 2-propylpentyl, cyclopentylmethyl, 2-cyclopentylethyl, cyclohexylmethyl, (S)-1-cyclohexylethyl, cycloheptylmethyl, (bicyclo[2.2.1]hept-2-yl)methyl, benzyl, (S)-1-phenylethyl, 2-phenylethyl, (S)-2-phenylpropyl, (R)-2-phenylpropyl, (2-fluorophenyl)methyl, (2-methylphenyl) methyl, (3,5-dimethylphenyl)methyl, 1-naphthylmethyl, 2-furanylmethyl, 3-furanylmethyl, 2-thienylmethyl, (3-methyl-2-thienyl)methyl or 2-thiazoylmethyl; $R^2$ is propyl, cyclopropylmethyl, 1H-imidazol-4-ylmethyl, (1-methyl-1H-imidazol-4-yl)methyl, 2-thienylmethyl, 2-oxozolylmethyl, 4-oxazolylmethyl, 2-thiazolylmethyl, 4-thiazolylmethyl, (2-methyl-4-thiazolyl)methyl or (2-amino-4-thiazolyl)methyl; and B is [1(S)-(cyclohexylmethyl)-2(S)-hydroxy-5-methylhexyl]amino, [1(S)-(cyclohexylmethyl)-2(S)-hydroxy-(3-cyclopropylpropyl)]amino, [1(S)-(cyclohexylmethyl)-2(R),3(S)-dihydroxy-(3-cyclopropylpropyl)]amino, [1(S)-(cyclohexylmethyl)-2(R),3(S)-dihydroxy-5-methylhexyl] amino, [1(S)-(cyclohexylmethyl)-2(R)-hydroxy-3-(1-methylethoxy)-3-oxopropyl]amino or [1(S)-cyclohexylmethyl)-2(S)-hydroxy-2-(1,5,5-trimethyl-2-oxopyrrolidin-3(S)-yl)ethyl]amino; or a pharmaceutically acceptable acid addition salt thereof.

5. The method as recited in claim 1 comprising administering the compound of formula 1 selected from the group consisting of:

$N^4$-benzyl-$N^4$-(2-morpholino-2-oxoethyl)-$N^1$-[1(S)-(cyclohexylmethyl)-2(R),3(S)-dihydroxy-5-methylhexyl]-2(R)-(cyclopropylmethyl) butanediamide, $N^4$-benzyl-$N^4$-[2(dimethylamino)-2-oxoethyl]-$N^1$-[1(S)-(cyclohexylmethyl)-2(R),3(S)-dihydroxy-5-methylhexyl]-2(R)-(cyclopropylmethyl) butanediamide, $N^4$-[2-(dimethylamino)-2-oxoethyl]-$N^4$-(2-phenylethyl)-$N^1$-[1(S)-(cyclohexylmethyl)-2(R),3(S)-dihydroxy-5-methylhexyl]-2(R)-(cyclopropylmethyl) butanediamide, $N^4$-[2-(dimethylamino)-2-oxoethyl]-$N^4$-(3-phenylpropyl)-$N^1$-[1(S)-(cyclohexylmethyl)-2(R),3(S)-dihydroxy-5-methylhexyl]-2(R)-(cyclopropylmethyl)-butanediamide, $N^4$-benzyl-$N^4$-{2-[methyl(1,1-dimethylethyl)amino]-2-oxoethyl}-$N^1$-[1(S)-(cyclohexylmethyl)-2(R),3(S)-dihydroxy-5-methylhexyl]-2(R)-(cyclopropylmethyl) butanediamide, $N^4$-benzyl-$N^4$-[2-(methylamino)-2-oxoethyl]-$N^1$-[1(S)-(cyclohexylmethyl)-2(R),3(S)-dihydroxy-5-methylhexyl]-2(R)-(cyclopropylmethyl) butanediamide, $N^4$-(2-amino-2-oxoethyl)-$N^4$-benzyl-$N^1$-[1(S)-(cyclohexylmethyl)-2(R),3(S)-dihydroxy-5-methylhexyl]-2(R)-(cyclopropylmethyl) butanediamide, $N^4$-benzyl-$N^4$-{2-[(methoxy)methylamino]-2-oxoethyl}-$N^1$-[1(S)-(cyclohexylmethyl)-2(R),3(S)-dihydroxy-5-methylhexyl]-2(R)-(cyclopropylmethyl) butanediamide, $N^4$-[2-(dimethylamino)-2-oxoethyl]-$N^4$-(1-naphthylmethyl)-$N^1$-[1(S)-(cyclohexylmethyl)-2(R),3

(S)-dihydroxy-5-methylhexyl]-2(R)-(cyclopropylmethyl)butanediamide,

N⁴-[2-(dimethylamino)-2-oxoethyl]-N⁴-[(4-methoxyphenyl)methyl]-N¹-[1(S)-(cyclohexylmethyl)-2(R),3(S)-dihydroxy-5-methylhexyl]-2(R)-(cyclopropylmethyl)butanediamide, N⁴-benzyl-N⁴-[2-(diethylamino)-2-oxoethyl]-N¹-[1(S)-(cyclohexylmethyl)-2(R),3(S)-dihydroxy-5-methylhexyl]-2(R)-(cyclopropylmethyl)butanediamide, N⁴-benzyl-N⁴-{2-{methyl[2-(2-pyridinyl)ethyl]amino}-2-oxoethyl}-N¹-[1(S)-(cyclohexylmethyl)-2(R),3(S)-dihydroxy-5-methylhexyl]-2(R)-(cyclopropylmethyl)-butanediamide, N⁴-[2-(dimethylamino)-2-oxoethyl]-N⁴-(2-pyridinylmethyl)-N¹-[1(S)-(cyclohexylmethyl)-2(R),3(S)-dihydroxy-5-methylhexyl]-2(R)-(cyclopropylmethyl)-butanediamide, N⁴-[2-(dimethylamino)-2-oxoethyl]-N⁴-(3-pyridinylmethyl)-N¹-[1(S)-(cyclohexylmethyl)-2(R),3(S)-dihydroxy-5-methylhexyl]-2(R)-(cyclopropylmethyl)butanediamide, N⁴-{2-{methyl{2-[methyl(morpholinocarbonyl)amino]ethyl}amino}-2-oxoethyl}-N⁴-[1(S)-phenylethyl]-N¹-[1(S)-(cyclohexylmethyl)-2(R),3(S)-dihydroxy-5-methylhexly]-2(R)-[(2-amino-4-thiazoly)methyl]butanediamide, N⁴-[2-(dimethylamino)-2-oxoethyl]-N⁴-[1(R)-phenylethyl]-N¹-[1(S)-(cyclohexylmethyl)-2(R),3(S)-dihydroxy-5-methylhexyl]-2(R)-(cyclopropylmethyl)butanediamide, N⁴-[2-(dimethylamino)-2-oxoethyl]-N⁴-[1(S)-phenylethyl]-N¹-[1(S)-(cyclohexylmethyl)-2(R),3(S)-dihydroxy-5-methylhexyl]-2(R)-(cyclopropylmethyl)-butanediamide, N⁴-[2-(dimethylamino)-2-oxoethyl]-N⁴-[1(S)-(1-naphthyl)ethyl]-N¹-[1(S)-(cyclohexylmethyl)-2(R),3(S)-dihydroxy-5-methylhexyl]-2(R)-(cyclopropylmethyl)butanediamide, N⁴-[2-(dimethylamino)-2-oxoethyl]-N⁴-[2(R)-phenylpropyl]-N¹-[1(S)-(cyclohexylmethyl)-2(R),3(S)-dihydroxy-5-methylhexyl]-2(R)-(cyclopropylmethyl)-butanediamide, N⁴-[2-(dimethylamino)-2-oxoethyl]-N⁴-[2(S)-phenylpropyl]-N¹-[1(S)-(cyclohexylmethyl)-2(R),3(S)-dihydroxy-5-methylhexyl]-2(R)-(cyclopropylmethyl)-butanediamide, N⁴-[2-(dimethylamino)-2-oxoethyl]-N⁴-(2-methyl-2-phenylpropyl)-N¹-[1(S)-(cyclohexylmethyl)-2(R),3(S)-dihydroxy-5-methylhexyl]-2(R)-(cyclopropylmethyl)-butanediamide, N⁴-[1(S)-phenylethyl]-N⁴-{2-{methyl[2-(2-pyridinyl)ethyl]amino}-2-oxoethyl}-N¹-[1(S)-(cyclohexylmethyl)-2(R),3(S)-dihydroxy-5-methylhexyl]-2(R)-(cyclopropylmethyl)butanediamide, N⁴-{2-{[2-(dimethylamino)ethyl]methylamino}-2-oxoethyl}-N⁴-[1(S)-phenylethyl]-N¹-[1(S)-(cyclohexylmethyl)-2(R),3(S)-dihydroxy-5-methylhexyl]-2(R)-(cyclopropylmethyl)butanediamide, N⁴-{2-{[2-(diethylamino)ethyl]methylamino}-2-oxoethyl}-N⁴-[1(S)-phenylethyl]-N¹-[1(S)-(cyclohexylmethyl)-2(R),3(S)-dihydroxy-5-methylhexyl]-2(R)-(cyclopropylmethyl)butanediamide, N⁴-[2-(dimethylamino)-2-oxoethyl]-N⁴-[1(S)-phenylethyl]-N¹-[1(S)-(cyclohexylmethyl)-2(R),3(S)-dihydroxy-5-methylhexyl]-2(R)-propylbutanediamide, N⁴-benzyl-N⁴-{2-{methyl[2-(2-pyridinyl)ethyl]amino}-2-oxoethyl}-N¹-[1(S)-(cyclohexylmethyl)-2(R),3(S)-dihydroxy-5-methylhexyl]-2(R)-propylbutanediamide, N⁴-[2-(dimethylamino)-2-oxoethyl]-N⁴-[1(S)-phenylethyl]-N¹-[1(S)-(cyclohexylmethyl)-2(R),3(S)-dihydroxy-5-methylhexyl]-2(R)-(1H-imidazol-4-ylmethyl)butanediamide, N⁴-[2-(dimethylamino)-2-oxoethyl]-N⁴-[1(S)-phenylethyl]-N¹-[1(S)-(cyclohexylmethyl)-2(R),3(S)-dihydroxy-5-methylhexyl]-2(R)-[(2-amino-4-thiazolyl)methyl]butanediamide, N⁴-benzyl-N⁴-{2-{methyl[2-(4-pyridinyl)ethyl]amino}-2-oxoethyl}-N¹-[1(S)-(cyclohexylmethyl)-2(R),3(S)-dihydroxy-5-methylhexyl]-2(R)-(cyclopropylmethyl)butanediamide, N⁴-[2-(dimethylamino)-2-oxoethyl]-N⁴-[1(S)-phenylethyl]-N¹-[1(S)-(cyclohexylmethyl)-2(R),3(S)-dihydroxy-5-methylhexyl]-2(R)-(4-thiazolylmethyl)butanediamide, N⁴-(cyclohexylmethyl)-N⁴-[2-(dimethylamino)-2-oxoethyl]-N¹-[1 (S)-(cyclohexylmethyl)-2(R),3(S)-dihydroxy-5-methylhexyl]-2(R)-(cyclopropylmethyl)butanediamide, N⁴-[2-(dimethylamino)-2-oxoethyl]-N⁴-[1(S)-phenylethyl]-N¹-[1-(S)-(cyclohexylmethyl)-2(R),3(S)-dihydroxy-5-methylhexyl]-2(S)-(2-thienylmethyl)butanediamide, N⁴-[1(S)-phenylethyl]-N⁴-(2-morpholino-2-oxoethyl)-N¹-[1(S)-(cyclohexylmethyl)-2 (R),3(S)-dihydroxy-5-methylhexyl]-2(R)-(cyclopropylmethyl)butanediamide, N⁴-benzyl-N⁴-{2-{methyl[2-(2-pyridinyl)ethyl]amino}-2-oxoethyl}-N¹-[1(S)-(cyclohexylmethyl)-2(R),3(S)-dihydroxy-5-methylhexyl]-2(S)-(2-thienylmethyl)butanediamide, N⁴-(cyclohexylmethyl)-N⁴-(2-morpholino-2-oxoethyl)-N¹-[1(S)-(cyclohexylmethyl)-2(R),3(S)-dihydroxy-5-methylhexyl]-2(R)-(cyclopropylmethyl)butanediamide, N⁴-(cyclohexylmethyl)-N⁴-[2-(dimethylamino)-2-oxoethyl]-N¹-[1(S)-(cyclohexylmethyl)-2(R),3(S)-dihydroxy-5-methylhexyl]-2(R)-(4-thiazolylmethyl)butanediamide, N⁴-(cyclohexylmethyl)-N⁴-[2-(dimethylamino)-2-oxoethyl]-N¹-[1(S)-(cyclohexylmethyl)-2(R),3(S)-dihydroxy-5-methylhexyl]-2(S)-(2-thiazolylmethyl)butanediamide, N⁴-(1(S)-cyclohexylethyl)-N⁴-[2-(dimethylamion)-2-oxoethyl]-N¹-[1(S)-(cyclohexylmethyl)2(R),3(S)-dihydroxy-5-methylhexyl]-2(R)-(cyclopropylmethyl)butanediamide, N⁴-(cyclohexylmethyl)-N⁴-(2-morpholino-2-oxoethyl)-N¹-[1(S)-(cyclohexylmethyl)-2 (R),3(S)-dihydroxy-5-methylhexyl]-2(S)-(2-thiazolylmethyl)butanediamide, N⁴-[2-(dimethylamino)-2-oxoethyl]-N⁴-[2(S)-phenylpropyl]-N¹-[1 (S)-(cyclohexylmethyl)-2(R),3(S)-dihydroxy-5-methylhexyl]-2(S)-(2-thiazolylmethyl)butanediamide, N⁴-benzyl-N⁴-{2-{methyl[2-(2-pyridinyl)ethyl]amino}-2-oxoethyl}-N¹-[1(S)-(cyclohexylmethyl)-2(R),3(S)-dihydroxy-5-methylhexyl]-2(S)-(2-thiazolymethyl)butanediamide, N$^4$-[2-(dimethylamino)-2-oxoethyl]-N$^4$-[1(S)-phenylethyl]-N$^1$-[1(S)-(cyclohexylmethyl)-2(S)-hydroxy-2-(1,5,5-trimethyl-2-oxopyrrolidin-3(S)-yl)ethyl]-2 (R)-(cyclopropylmethyl)butanediamide, N$^4$-[2-(dimethylamino)-2-oxoethyl]-N$^4$-[1(S)-phenylethyl]-N$^1$-[1(S)-(cyclohexylmethyl)-2(R),3(S)-dihydroxy-(3-cyclopropylpropyl)]-2(R)-[(2-amino-4-thiazolyl)methyl]butanediamide, N$^4$-[2-(dimethylamino)-2-oxoethyl]-N$^4$-[1(S)-phenylethyl]-N$^1$-[1(S)-(cyclohexylmethyl)-2(S)-hydroxy-2-(1,5,5-trimethyl-2-oxopyrrolidin-3(S)-yl)ethyl]-2(R)-[(2-amino-4-thiazolyl)methyl]butanediamide, N$^4$-[2-(dimethylamino)-2-oxoethyl]-N$^4$-[1(S)-phenylethyl]-N$^1$-[1(S)-(cyclohexylmethyl)-2(R)-hydroxy-3-(1-methylethoxy)-3-oxopropyl]-2(R)-[2-amino-4-thiazolyl)methyl]butanediamide, N$^4$-(cyclohexylmethyl)-N$^4$-{2-{methyl-[2-(2-pyridinyl)ethyl]amino}-2-oxoethyl }-N$^1$-[1(S)-(cyclohexylmethyl)-2(R),3(S)-dihydroxy-5-methylhexyl]-2(R)-(cyclopropylmethyl)butanediamide, N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-[(2-methyl-4-thiazolyl)methyl]-butanediamide, N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-[(2-amino-4-thiazolyl)methyl]butanediamide, N$^4$-(cyclohexylmethyl)-N$^4$-(2-morpholino-2-oxoethyl)-N$^1$-[1(S)-(cyclohexylmethyl)-2 (R),3(S)-dihydroxy-5-methylhexyl]-2(R)-[(2-amino-4-thiazolyl)methyl]-butanediamide, N$^4$-(cyclohexylmethyl)-N$^4$-{2-{methyl[2-(2-pyridinyl)ethyl]amino}-2-oxoethyl }-N$^1$-[1-(S)-(cyclohexylmethyl)-2(R),3(S)-dihydroxy-5-methylhexyl]-2(R)-[(2-amino-4-thiazolyl)methyl]butanediamide, N$^4$-[2-(dimethylamino)-2-oxoethyl]-N$^4$-[2-(2-pyridinyl)ethyl]-N$^1$-[1(S)-(cyclohexylmethyl)-2(R),3(S)-dihydroxy-5-methylhexyl]-2(R)-(cyclopropylmethyl)butanediamide, N$^4$-benzyl-N$^4$-[2-(dimethylamino)-2-oxoethyl]-N$^1$-[1(S)-(cyclohexylmethyl)-2 (R),3(S)-dihydroxy-5-methylhexyl]-2(R)-[(2-amino-4-thiazolylmethyl]butanediamide, N$^4$-benzyl-N$^4$-{2-{methyl[2-(2-pyridinyl)ethyl]amino}-2-oxoethyl}-N$^1$-[1(S)-(cyclohexylmethyl)2(R),3(S)-dihydroxy-5-methylhexyl]-2(R)-(4-thiazolylmethyl)butanediamide, N$^4$-[2-(dimethylamino)-2-oxoethyl]-N$^4$-[1(S)-phenylethyl]-N$^1$-[1(S)-(cyclohexylmethyl)-2(R),3(S)-dihydroxy-5-methylhexyl]-2(S)-(2-thiazolylmethyl)butanediamide, N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(phenylmethyl)butanediamide, N$^4$-{{1(S),2(R),4(S)- and 1(R),2(S),4(R)-{bicyclo[2.2.1]hept-2-yl}methyl}-N$^4$-[2-(dimethylamino)-2-oxoethyl]-N$^1$-[1-(S)-(cyclohexylmethyl)-2(R),3 (S)-dihydroxy-5-methylhexyl]-2(R)-(4-thiazolylmethyl)butanediamide, N$^4$-benzyl-N$^4$-{2-{methyl[2-(2-pyridinyl)ethyl]amino}-2-oxoethyl}-N$^1$-[1(S)-(cyclohexylmethyl)-2(R),3(S)-dihydroxy-5-methylhexyl]-2(R)-[(2-amino-4-thiazolyl)methyl]butanediamide, N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(3-pyridinylmethyl)butanediamide, N$^4$-(cyclohexylmethyl)-N$^4$-(2-morpholino-2-oxoethyl)-N$^1$-[1(S)-(cyclohexylmethyl)-2(R),3(S)-dihydroxy-5-methylhexyl]-2(R)-(3-pyridinylmethyl)butanediamide, N$^4$-[2-(dimethylamino)-2-oxoethyl]-N$^4$-(2-phenylethyl)-N$^1$-[1(S)-(cyclohexylmethyl)-2(R),3(S)-dihydroxy-5-methylhexyl]-2(R)-[(2-amino-4-thiazolyl)methyl]butanediamide, N$^4$-[2-(dimethylamino)-2-oxoethyl]-N$^4$-[2(S)-phenylpropyl]-N$^1$-[1(S)-(cyclohexylmethyl)-2(R),3(S)-dihydroxy-5-methylhexyl]-2(R)-[(2-amino-4-thiazolyl)methyl]butanediamide, N$^4$-{2-[4-(methoxymethoxy)piperidin-yl]-2-oxoethyl}-N$^4$-[cyclohexyl-methyl]-N$^1$-[1(S)-(cyclohexylmethyl)-2(R),3(S)-dihydroxy-5-methylhexyl]-2(R)-[(2-amino-4 -thiazoly)methyl]-butanediamide, N$^4$-[1(S)-cyclohexylethyl]-N$^4$-{2-{methyl[2-(2-pyridinyl)ethyl]amino }-2-oxoethyl}-N$^1$-[1(S)-(cyclohexylmethyl)-2(R),3(S)-dihydroxy-5-methylhexyl]-2(R)-[(2-amino-4-thiazolyl)methyl]butanediamide, N$^4$-[2-(dimethylamino)-2-oxoethyl]-N$^4$-(2-pyridinylmethyl)-N$^1$-[1(S)-(cyclohexylmethyl)-2(R),3(S)-dihydroxy-5-methylhexyl]-2(R)-[(2-amino-4 -thiazolyl)methyl]butanediamide, N$^4$-(cyclohexylmethyl)-N$^4$-{2-{methyl[2-(2-pyridinyl)ethyl]amino}-2-oxoethyl }N$^1$-{1(S)-(cyclohexylmethyl)-2(R)-hydroxy-3-[(1-methyl-1H-tetrazol-5-yl)-thio]propyl}-2(R)-[(2-amino-4-thiazolyl)methyl]butanediamide, N$^4$-(cyclohexylmethyl)-N$^4$-{2-{methyl[2-(2-pyridinyl)ethyl]amino}-2-oxoethyl }-N$^1$-[1(S)-(cyclohexylmethyl)-2(R),3(S)-dihydroxy-5-methylhexyl]-2(R)-(3-pyridinylmethyl)butanediamide, N$^4$-(cyclohexylmethyl)-N$^4$-(2-morpholino-2-oxoethyl)-N$^1$-[1(S)-(cyclohexylmethyl)-2(R),3(S)-dihydroxy-5-methylhexyl]-2(R)-(2-pyridinylmethyl)butanediamide, N$^4$-(cyclohexylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(2-pyridinylmethyl)butanediamide, N$^4$-(cyclopentylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(3-pyridinylmethyl)butanediamide, N$^4$-(cycloheptylmethyl)-N$^4$-[2-(dimethylamino)-2-oxoethyl]-N$^1$-[1(S)-(cyclohexylmethyl)-2(R),3(S)-dihydroxy-5-methylhexyl]-2(R)-(3-pyridinylmethyl)butanediamide, N$^4$-(cyclopentylmethyl)-N$^4$-{2-{methyl[2-(2-pyridinyl)ethyl]amino}-2-oxoethyl ]-N$^1$-[1(S)-(cyclohexylmethyl)-2(R),3(S)-dihydroxy-5-methylhexyl]-2(R)-[(2-amino-4-thiazolyl)methyl]butanediamide, N$^4$-{2-{methyl[2-(2-pyridinyl)ethyl]-amino}-2-oxoethyl}-N$^4$-(2-thienylmethyl)-N$^1$-[1(S)-(cyclohexylmethyl)-2(R),3(S)-dihydroxy-5-methylhexyl]-2(R)-[(2-amino-4-thiazolyl)methyl]butanediamide, $N^4$-[2-(dimethylamino)-2-oxoethyl]-$N^4$-[(3,5-dimethylphenyl)methyl]-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(cyclohexylmethyl)-$N^4$-{2-{methyl[2-(2-pyridinyl)ethyl]amino}-2-oxoethyl}-$N^1$-[1(S)-(cyclohexylmethyl)-2(R)-hydroxy-3-(1-methylethoxy)-3-oxopropyl]-2(R)-[(2-amino-4-thiazolyl)methyl]butanediamide, $N^4$-{2-{methyl[2-(2-pyridinyl)ethyl]amino}-2-oxoethyl}-$N^4$-[1(S)-phenylethyl]-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(cyclohexylmethyl)-$N^4$-{2-{methyl[2-(3-pyridinyl)ethyl]amino}-2-oxoethyl}-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(cyclohexylmethyl)-$N^4$-{2-{methyl[2-(2-pyridinyl)ethyl]amino}-2-oxoethyl}-$N^1$-[1(S)-(cyclohexylmethyl)-2(S)-hydroxy-5-methylhexyl]-2(R)-[(2-amino-4-thiazolyl)methyl]butanediamide, $N^4$-(cycloheptylmethyl)-$N^4$-[2-(dimethylamino)-2-oxoethyl]-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(2-furanylmethyl)-$N^4$-{2-{methyl-[2-(2-pyridinyl)ethyl]amino}-2-oxoethyl}-$N^1$-[1(S)-(cyclohexylmethyl)-2(R),3(S)-dihydroxy-5-methylhexyl]-2(R)-[(2-amino-4-thiazolylmethyl]butanediamide, $N^4$-(cyclopentylmethyl)-$N^4$-(2-morpholino-2-oxoethyl)-$N^1$-[1(S)-(cyclohexylmethyl)-2(R), 3(S)-dihydroxy-5-methylhexyl]-2(R)-[(2-amino-4-thiazolyl)methyl]butanediamide, $N^4$-(cycloheptylmethyl)-$N^4$-{2-{methyl[2-(2-pyridinyl)ethyl]amino}-2-oxoethyl}-$N^1$-[1(S)-(cyclohexylmethyl)-2(R),3(S)-dihydroxy-5-methylhexyl]-2(R)-[(2-amino-4-thiazolyl)methyl]butanediamide, $N^4$-[2-fluorophenyl)methyl]-$N^4$-{2-{methyl[2-(2-pyridinyl)ethyl]amino}-2-oxoethyl}-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(cyclohexylmethyl)-$N^4$-{2-{methyl{2-[methyl(morpholinocarbonyl)amino]ethyl}amino}-2-oxoethyl}-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(2-ethylbutyl)-$N^4$-{2-{methyl[2-(2-pyridinyl)ethyl]amino}-2-oxoethyl}-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(cyclopentylmethyl)-$N^4$-[2-dimethylamino)-2-oxoethyl]-$N^1$-[1(S)-(cyclohexylmethyl)-2(R),3(S)-dihydroxy-5-methylhexyl]-2(R)-[(2-amino-4-thiazolyl)methyl]butanediamide, $N^4$-{2-{methyl[2-(2-pyridinyl)ethyl]amino}-2-oxoethyl}-$N^4$-(2-thiazolylmethyl)-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(2-cyclopentylethyl)-$N^4$-{2-{methyl[2-(2-pyridinyl)ethyl]amino}-2-oxoethyl}-$N^1$-[1(S)-(cyclohexylmethyl)-2(R),3(S)-dihydroxy-5-methylhexyl]-2(R)-[(2-amino-4-thiazolyl)methyl]butanediamide, $N^4$-{2-{methyl[2-(2-pyridinyl)ethyl]amino}-2-oxoethyl}-$N^4$-[(3-methyl-2-thienyl)methyl]-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(3-furanylmethyl)-$N^4$-{2-{methyl-[2-(2-pyridinyl)ethyl]amino}-2-oxoethyl}-$N^1$-[1(S)-(cyclohexylmethyl)-2(R),3(S)-dihydroxy-5-methylhexyl]-2(R)-[(2-amino-4-thiazolyl)methyl]butanediamide, $N^4$-(cyclohexylmethyl)-$N^4$-{2-[methyl-(2-morpholinoethyl)amino]-2-oxoethyl}-$N^1$-[1(S)-(cyclohexylmethyl)-2(R),3(S)-dihydroxy-5-methylhexyl]-2(R)-[(2-amino-4-thiazolyl)methyl]butanediamide, $N^4$-{2-methyl[2-(2-pyridinyl)ethyl]amino}-2-oxoethyl}-$N^4$-(1-propylbutyl)-$N^1$-(cyclohexylmethyl)-2(R),3(S)-dihydroxy-5-methylhexyl]-2(R)-[(2-amino-4-thiazolyl)methyl]butanediamide, $N^4$-{2-{methyl[2-(2-pyridinyl)ethyl]amino}-2-oxoethyl}-$N^4$-(2-propylpentyl)-$N^1$-[1(S)-(cyclohexylmethyl)-2(R),3(S)-dihydroxy-5-methylhexyl]-2(R)-[(2-amino-4-thiazolyl)methyl]butanediamide, and $N^4$-{2-[methyl(2-morpholinoethyl)amino]-2-oxoethyl}-$N^4$-[1(S)-phenylethyl]-$N^1$-[1(S)-(cyclohexylmethyl)-2(R),3(S)-dihydroxy-5-methylhexyl]-2(R)-[(2-amino-4-thiazolyl)methyl]butanediamide.

* * * * *